United States Patent [19]

Shimizu et al.

[11] Patent Number: 5,391,741
[45] Date of Patent: Feb. 21, 1995

[54] SQUARYLIUM COMPOUND AND OPTICAL INFORMATION RECORDING MEDIUM USING THE SAME

[75] Inventors: Ikuo Shimizu; Hiroshi Toyoda, both of Yokkaichi; Yukiyoshi Ito; Tsutomu Sato, both of Tokyo, all of Japan

[73] Assignee: Kyowa Hakko Kogyo Co., Ltd., Tokyo, Japan

[21] Appl. No.: 51,411

[22] Filed: Apr. 23, 1993

[30] Foreign Application Priority Data

Apr. 24, 1992 [JP] Japan ................................. 4-106399
Apr. 24, 1992 [JP] Japan ................................. 4-106400

[51] Int. Cl.[6] .................. C07D 471/00; C07D 221/06; C07D 215/00
[52] U.S. Cl. .................................... 544/345; 544/234; 546/17; 546/101; 546/165; 546/166; 430/495
[58] Field of Search ............... 544/345, 101, 165, 166, 544/17, 234; 546/101, 165, 166

[56] References Cited

U.S. PATENT DOCUMENTS

| | | | |
|---|---|---|---|
| 5,085,909 | 2/1992 | Satoh et al. | 428/64 |
| 5,149,819 | 9/1992 | Satoh et al. | 548/149 |

FOREIGN PATENT DOCUMENTS

0408014A1 1/1991 European Pat. Off. .
3914151A1 11/1989 Germany .

OTHER PUBLICATIONS

"Preparation of squarylium compounds and optical recording media using them", Tsutomo Sato et al., Chemical Abstracts, vol. 116, 1992, Abstract No. 95903x.

"Optical recording medium using optical interference on recording layer interface", Tsutomu Sato et al., Chemical Abstracts, vol. 114, 1991, Abstract No. 52947f.

"Optical recording media", Tatsuya Sakaeda et al., Chemical Abstracts, vol. 114, 1991, Abstract No. 33199x.

"Optical recording media", Takeshi Santo et al., Chemical Abstracts, vol. 116, 1992, Abstract No. 72474u.

"Methine dyes", Akira Tanaka et al., Chemical Abstracts, vol. 117, 1992, Abstract No. 132904s.

*Primary Examiner*—Cecilia Tsang
*Attorney, Agent, or Firm*—Finnegan, Henderson, Farabow, Garrett & Dunner

[57] ABSTRACT

There are described a novel squarylium compound represented by the formula (I):

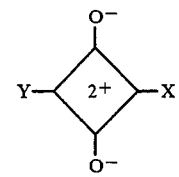

and an optical information recording medium using the squarylium compound in the recording layer.

7 Claims, 22 Drawing Sheets

SQUARYLIUM COMPOUND AND OPTICAL INFORMATION RECORDING MEDIUM USING THE SAME

FIELD OF THE INVENTION

The present invention relates to a squarylium compound and optical information recording medium using said compound which can be used in the optical recording field.

BACKGROUND OF THE INVENTION

As main use of near infrared absorbers is that of recording materials in optical information recording medium. As near infrared absorbers which are used as pigment of recording material, there are known, phenanthrene pigment, naphthoquinone pigment, pyrylium pigment and the like in addition to phthalocyanin pigment and cyanin pigment [see JP-A-97033, JP-A-58-83344, JP-A-58-224793, JP-A-58-214162 and JP-A-59-24692]. There are squarylium compounds used for optical information recording medium on which the present applicant has already filed [see JP-A-1-275188 and JP-A-3-188063].

The above described optical information recording media are direct read after write (DRAW) type. However, in addition to those, DRAW type CD has been recently exploited. This type of CD has such the characteristics that a user can record an information therein and the signal after recording can be reproduced by a commercially available CD player since it satisfies with the standards on the previous CD. As recording materials therefor, cyanin pigment and the like are proposed [see JP-A-63-224045, JP-A-2-42652].

However, the above described pigments as recording materials have a variety of problems and therefore optical information recording media using them also have the problems arising from the pigments.

Firstly, the phthalocyanin pigments have the problems that they have extremely low solubility in the organic solvents and can not be used for application by coating. Phenanthrene and naphthoquinone pigments have the problems that they have the lower reflectance in spite of the advantage of easy vacuum deposition. The lower reflectance results in the lower contrast on reflectance between recorded parts by the laser rays and non-recorded parts and therefore the lower reproductivity of the recorded information. Furthermore, the pyrylium and cyanin pigments have the problems that they have the inferior heat resistance and are liable to be deteriorated by the reproducing rays although they can be applied by coating.

OBJECTS OF THE INVENTION

The main object of the present invention is to provide a novel pigment compound which can overcome the problems of the above pigments.

The other object of the present invention is to provide a novel optical information recording medium which can overcome the disadvantages of the above optical information recording medium using the above pigments.

These objects as well as other objects and advantages of the present invention will become apparent to those skilled in the art from the following description with reference to the accompanying drawings.

SUMMARY OF THE INVENTION

Figure 1:
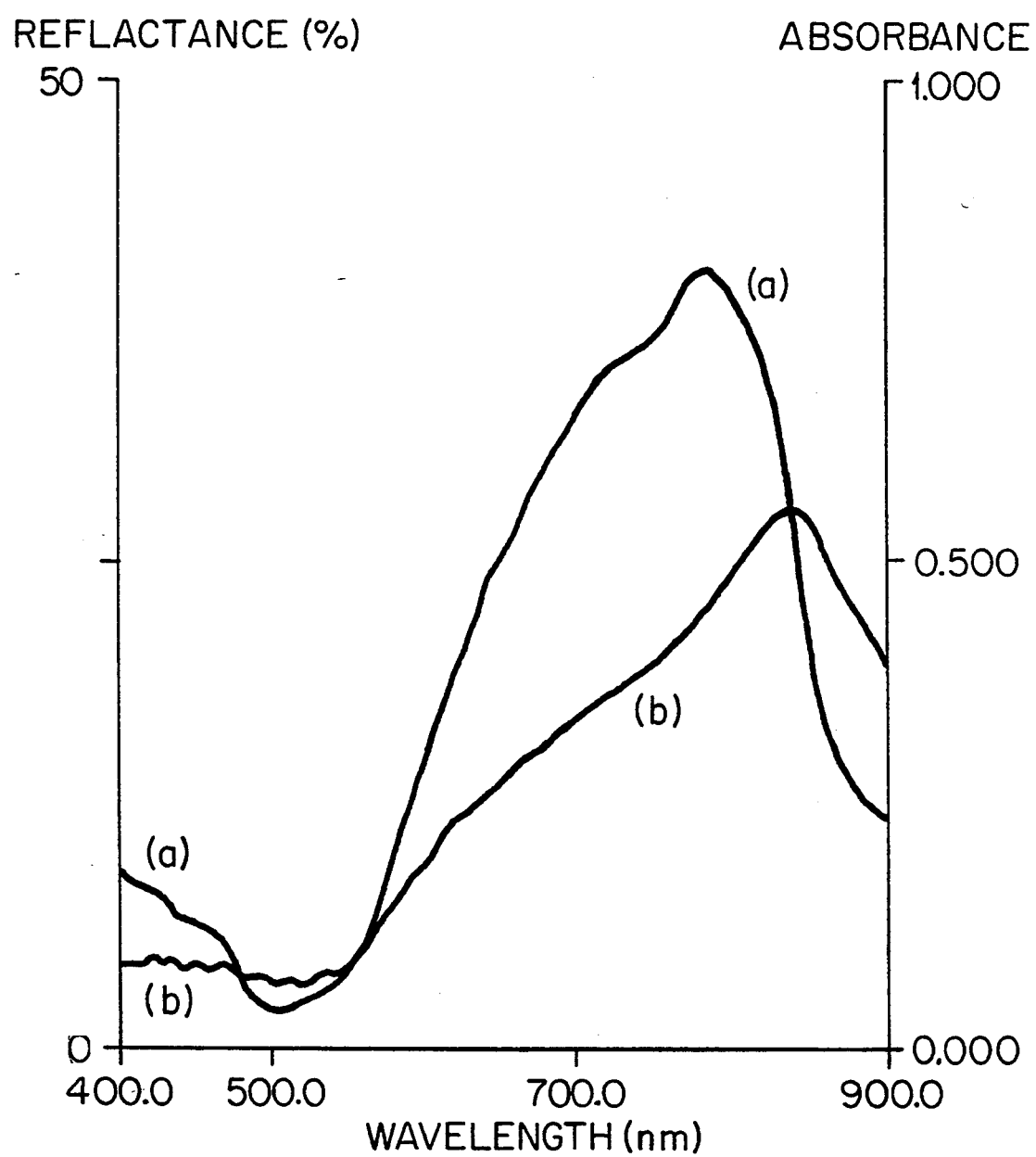
FIG. 1 is a chart showing the spectral properties of the recording medium obtained in Example 22 where the parallel rays are past through the base of the smooth part. (a) shows the absorption spectrum of the recording medium and (b) shows the reflection spectrum where the measuring was carried out through the base of the recording medium.

The present inventors have been studied extensively and, as the result, successfully synthesized the novel squarylium compounds, which have resulted in the findings that the compounds can overcome the above problems.

That is, the present invention provides a squarylium compound represented by the formula (I):

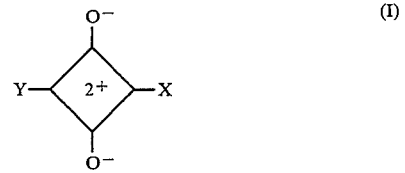

(I)

wherein (1) X represents the group (A):

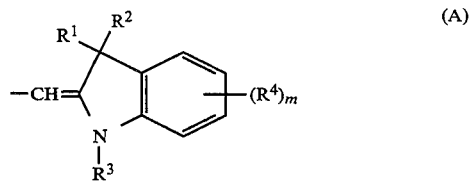

(A)

wherein $R^1$ and $R^2$ are the same or different and represent alkyl group, or $R^1$ and $R^2$ are taken together to form hydrocarbon ring, $R^3$ represents hydrogen atom, alkyl group or aryl group, $R^4$ represents halogen atom, alkyl group, aralkyl group, aryl group or alkoxy group, m represents an integer of 0 to 4, provided that when m represents 2 to 4, $R^4$'s may be the same or different or adjacent two $R^4$'s may form optionally substituted aromatic ring, and Y represents the group (B):

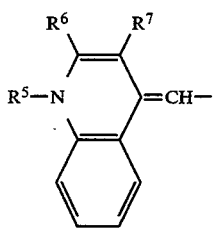

(B)

wherein $R^5$ represents alkyl group, $R^6$ and $R^7$ are the same or different and represent hydrogen, alkyl group or aralkyl group, or $R^6$ and $R^7$ are taken together to form optionally substituted aromatic ring or hydrocarbon ring, or (2) X represents the group (C):

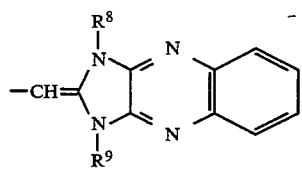

(C)

wherein $R^8$ and $R^9$ are the same or different and represent hydrogen atom, aralkyl group, alkyl group or aryl group, and Y represents the group (D):

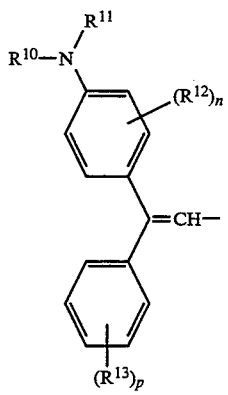

(D)

wherein $R^{10}$ and $R^{11}$ are the same or different and represent hydrogen, alkyl group, aralkyl group or aryl group, said aralkyl or aryl group being optionally substituted with one or more substituents, $R^{12}$ represents halogen atom, alkyl group, alkoxy group, nitro group or hydroxy group, n represents an integer of 0 to 4 provided that when n represents an integer of 0 to 4 provided that when n represents 2 to 4, $R^{12}$'s are the same or different, $R^{13}$ represents halogen atom, alkyl group, alkoxy group, hydroxy group, nitro group, cyano group, trifluoromethyl group or —$NQ^1Q^2$ (wherein $Q^1$ and $Q^2$ are the same or different and are as defined for $R^{10}$), p represents an integer of 0 to 5 provided that when p represents 2 to 5, $R^{13}$'s are the same or different, or Y represents the group (E):

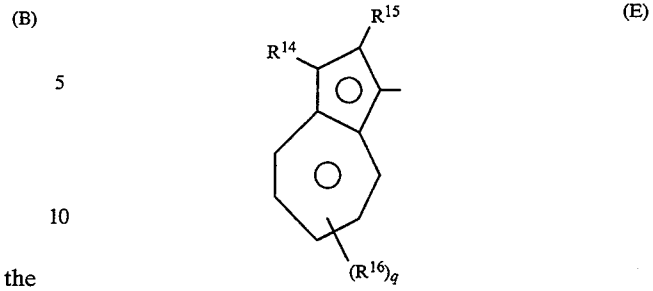

(E)

wherein $R^{14}$ and $R^{15}$ represent hydrogen atom, alkyl group, aralkyl group or aryl group, or $R^{14}$ and $R^{15}$ are taken together to form optionally substituted aromatic, heterocyclic or hydrocarbon ring, $R^{16}$ represents alkyl group, aralkyl group or aryl group, q represents an integer of 0 to 3 provided that when q represents 2 or 3, $R^{16}$'s are the same or different, or adjacent two $R^{16}$'s are taken together to form optionally substituted aromatic, heterocyclic or hydrocarbon ring, or Y represents the group (B)

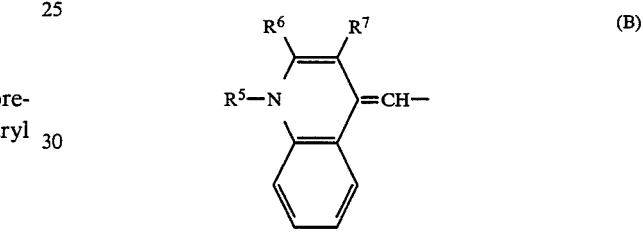

(B)

wherein $R^5$, $R^6$ and $R^7$ are the same as defined above.

The present invention also provided an optical information recording medium using said squarylium compound in the recording layer.

The squarylium compound of the present invention can be easily vacuum-deposited, has the high solubility in an organic solvent and the high absorbance in near infrared rays, and has excellent storage stability and high heat resistance. The optical information recording medium utilizing the squarylium compound has high reflectance, high contrast on reflectance, the excellent storage stability and stability to the reproducing rays. The recording medium of the present invention can be prepared utilizing vacuum deposition and solvent-coating method and therefore is expected to reduce the cost.

DETAILED DESCRIPTION OF THE INVENTION

As used herein, "compound (I)" refers to a squarylium compound represented by the formula (I). Like this, "compound (N)" refers to a squarylium compound represented by the formula (N).

When X represents the group (A) and (Y) represents the group (B), the definition of variable substituents are as follows:

Alkyl group and the alkyl part of alkoxy group represent the straight or branched alkyl having 1 to 4 carbon atoms, for example, methyl, ethyl, propyl, isopropyl, butyl, isobutyl, tert-butyl and the like.

Aralkyl group represents aralkyl having 7 to 10 carbon atoms, for example, benzyl, phenethyl, phenylpropyl and the like.

Aryl group represents, for example, phenyl, naphthyl and the like.

The alkylene or alkenylene part which forms the hydrocarbon ring represents alkylene or alkenylene chain having 3 to 6 carbon atoms, for example, propylene, butylene, betenylene, pentylene, pentenylene, hexylene, hexenylene, hexadienylene and the like.

Halogen represents chlorine, bromine, fluorine and the like.

Aromatic ring represents benzene ring and the like.

The examples of the substituents on the aromatic ring or hydrocarbon ring are halogen, arkyl group, aralkyl group, aryl group and the like which are described above.

When X represents the group (C) and Y represents the group (D), (E) or (B), the definition of the variable substituents are as follows:

Alkyl group or alkyl part of alkoxy group represent the straight or branched alkyl having 1 to 6 carbon atoms or cyclic alkyl group having 3 to 8 carbon atoms, for example, methyl, ethyl, n-propyl, isopropyl, n-butyl, isobutyl, sec-butyl, tert-butyl, n-amyl, isoamyl, sec-amyl, active amyl, tert-amyl, n-hexyl, cyclopropyl, cyclohexyl and the like.

Aralkyl group represents aralkyl having 7 to 10 carbon atoms, for example, benzyl, phenethyl, phenylpropyl and the like.

Aryl group represents, for example, phenyl, naphthyl and the like.

The examples of the substituents of aralky or aryl group are halogen atom, alkyl group, alkoxy group and the like.

Halogen represents chlorine, bromine, fluorine and the like. The alkyl group and the alkyl part of alkoxy are as defined above.

Aromatic ring represents benzene ring and the like.

The heterocyclic ring which is formed by $R^{14}$ and $R^{15}$ or the adjacent two $R^{16}$'s is heterocycle containing oxygen, nitrogen or sulfur. For example, $-R^{14}-R^{15}-$ or $-R^{16}-R^{13}-$ represents $-CH=CH-O-$, $-N=CH-S-$, $-CH=CH-S-$ and the like.

Alkylene or alkenylene part which forms the hydrocarbon ring represents alkylene or alkenylene chain having 3 to 6 carbon atoms, for example, propylene, butylene, bentenylene, pentylene, pentenylene, hexylene, hexenylene, hexadienylene and the like.

The examples of the substituents on aromatic heterocyclic or hydrocarbon ring are halogen atom, alkyl group, aralky group, aryl group and the which are as defined above.

Then, a process for preparation of the compound (I) is explained.

A squarylium compound (Ia) wherein X represents the group (A) and Y represents the group (B) can be prepared by reacting 3,4-diisopropoxy-3-cyclobuten-1,2-dione and a lepidinium derivative in an solvent in the presence of metallic sodium, hydrolyzing the resulting isopropoxycyclobutenedione derivative in the presence of an acid, and reacting under heating the resulting hydroxycyclobutenedione derivative with indoline 3H-indolium compound in a solvent, if necessary, in the presence of a base. Alternatively, the squarylium compound (I) wherein X represents the group (A) and Y represents the group (B) can be prepared according to the same manner as that described above except that 3,4-dichloro-3-cyclobuten-1,2-dione is used in the presence of a base in place of 3,4-diisopropoxy-3-cyclobuten-1,2-dione in the presence of metallic sodium and chlorocyclobutenedione is obtained in place of isopropoxycyclobutenedione. The reaction is shown in the following Reaction Scheme.

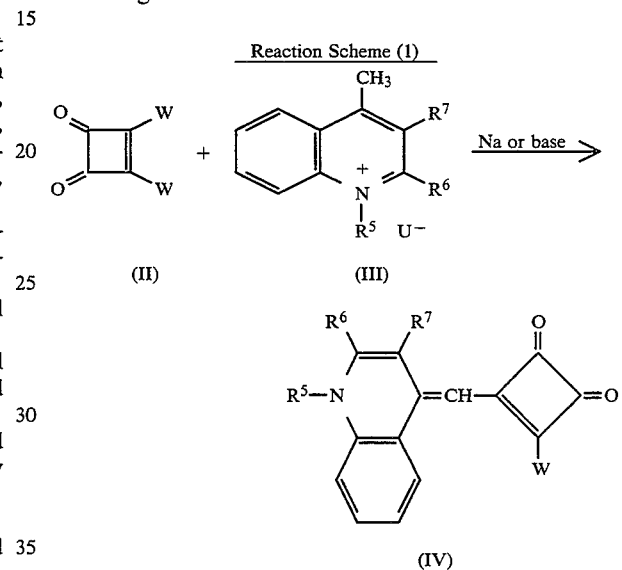

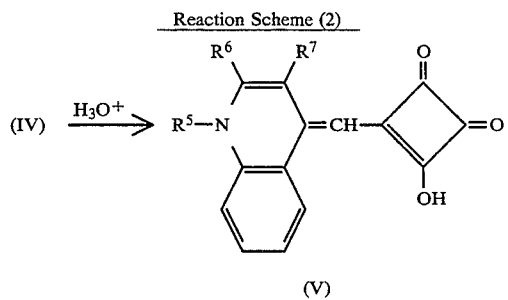

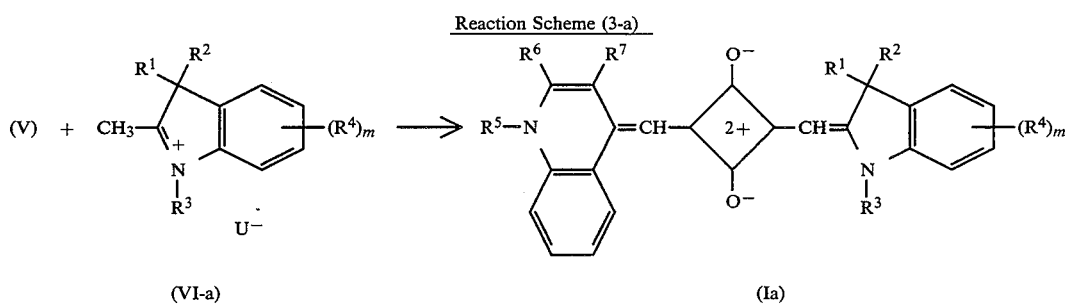

Reaction Scheme (3-b)

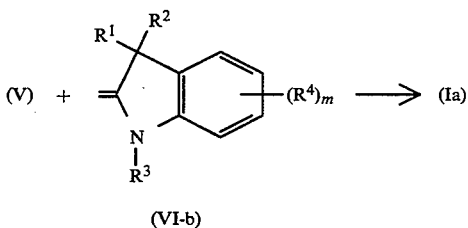

(VI-b)

In the above Reaction Schemes, $R^1$, $R^2$, $R^3$, $R^4$, $R^5$, $R^6$, $R^7$ and m are the same as defined above, U represents chlorine, bromine or iodine atom, and W represents isopropoxy group or chlorine atom.

The reaction (1) is carried out by reacting a compound (II) and the equivalent moles of a compound (III) at room temperature in a solvent which dose not inhibit the reaction in the presence of the equivalent amount of metallic sodium or the equivalent moles of or two times moles of a base. The reaction is completed in 3 to 6 hours when metallic sodium is used, or in 5 to 60 minutes when the base is used. The examples of the solvent to be used are alcoholic solvents, for example, methanol, ethanol, propanol, butanol and the like when metallic sodium is used. When the base is used, the examples of the solvent are chloroform, dichlormethane, 1,2-dichlorethane, diethyl ether, tetrahydrofuran, toluene, benzene, dimethylformamide, dimethyl sulfoxide and the like. As the base, the organic bases such as pyridine, quinoline, triethylamine and the like are used. After completion of the reaction, if any, the insolubles are removed by filtration and the solvent is distilled off from the reaction solution to give a compound (IV).

The reaction (2) is carried out by heating the compound (IV) at 90° to 110° C. for 5 to 20 hours in a 50 to 90 (wt.) % aqueous solution of acetic acid. The solvent is then distilled off to give a compound (V).

The reaction (3) is carried out by heating the compound (V) and the equivalent moles of 3H-indolium derivative (VI-a) or indoline derivative (VI-b) at 90° to 110° C. in a solvent, if necessary, in the presence of the equivalent moles of a base. The reaction is completed in 1 to 5 hours. As the solvent, an alcoholic solvent having 4 to 6 carbon atoms can be used sole or in admixture with benzene or toluene (alcohol is not less than 50%). As the base to be used, there are the organic bases such as pyridine, quinoline, triethylamine and the like.

After the above reaction, the product is isolated by column chromatography to give a compound (Ia).

A squarylium compound (Ib) wherein X represents the group (C) and Y represents the group (D) can be prepared by reacting 3,4-dichloro-3-cyclobuten-1,2-dione and 1-diarylethylene compound in a solvent, removing the solvent, hydrolyzing the resulting residue, and reacting the hydrolyzed product and imidazoquinoxalinium derivative in the presence of a base. The reaction is shown by the following Reaction Schemes.

Reaction Scheme (4)

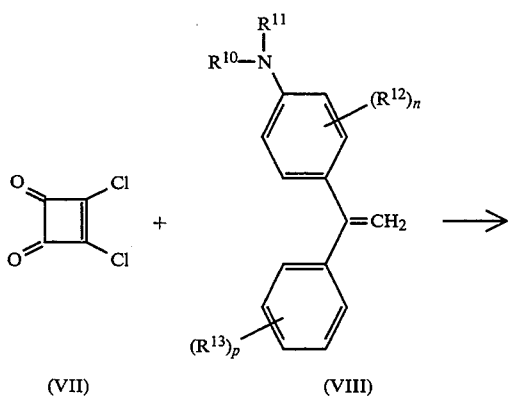

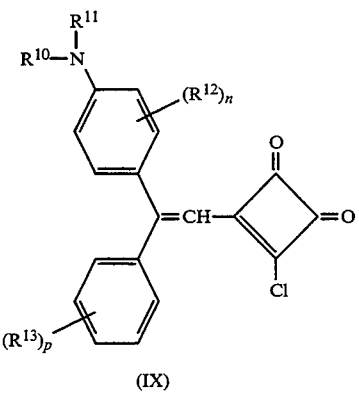

Reaction Scheme (5)

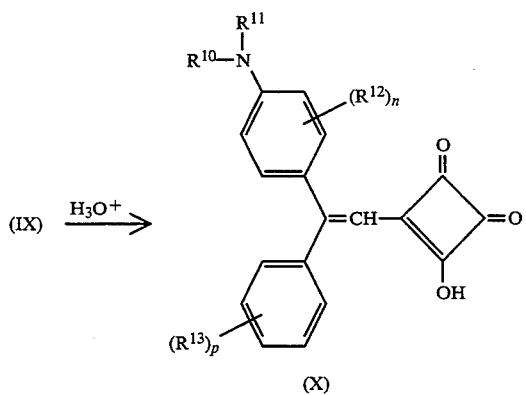

Reaction Scheme (6)

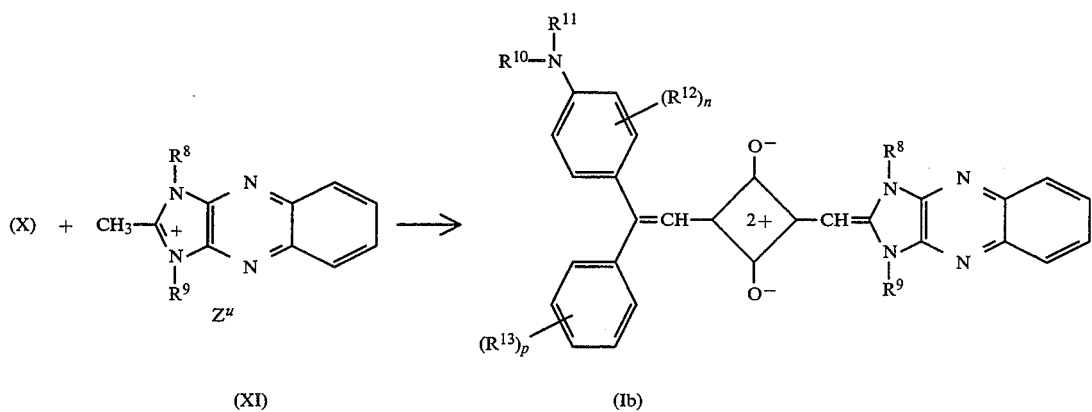

In the above Reaction Schemes, $R^8$, $R^9$, $R^{10}$, $R^{11}$, $R^{12}$, $R^{13}$, n and p are the same as defined above, and Z represents chlorine, bromine or iodine atom.

The reaction (4) is carried out by reacting a compound (VII) and the equivalent amount of a compound (VIII) at room temperature in a solvent which can dissolve these compound and dose not inhibit the reaction. The reaction is completed in 5 to 60 minutes.

As the solvent to be used, there are chloroform, dichloromethane, 1,2-dichloroethane, diethyl ether, tetrahydrofuran, toluene, benzene, dimethylformamide, dimethyl sulfoxide and the like. The solvent is distilled off from the reaction mixture to give the crude product of a compound (IX).

The reaction (5) can be carried out by heating the compound (IX) at 90° to 110° C. in a 50 to 90 (wt.) % aqueous solution of acetic acid. The reaction is completed in 1 to 20 hours. The solvent is distilled off to give the crude product of a compound (X).

The reaction (6) can be carried out by reacting the compound (X) and the equivalent moles of imidazoquinoxalinium derivative (XI) at 90° to 110° C. in a solvent in the presence of the equivalent moles of a base. The reaction is completed in 1 to 5 hours. As the base to be used, there are the organic bases such as pyridine, quinoline, triethylamine and the like.

As the solvent, an alcoholic solvent having 4 to 6 carbon atoms can be used sole or in admixture with benzene or toluene (alcohol is not less than 50%). After the reaction, the product is isolated by column chromatography to give a compound (Ib).

A squarylium compound (Ic) wherein X represents the group (C) and Y represents the group (E) can be prepared by reacting 3,4-dichloro-3-cyclobuten-1,2-dione and azulene derivative, hydrolyzing the resulting chlorocyclobutenedione derivative, and reacting the resulting hydroxycyclobutenedione derivative with imidazoquinoxalinium derivative in the presence of a base. The reaction is shown in the following Reaction Schemes.

Reaction Scheme (7)

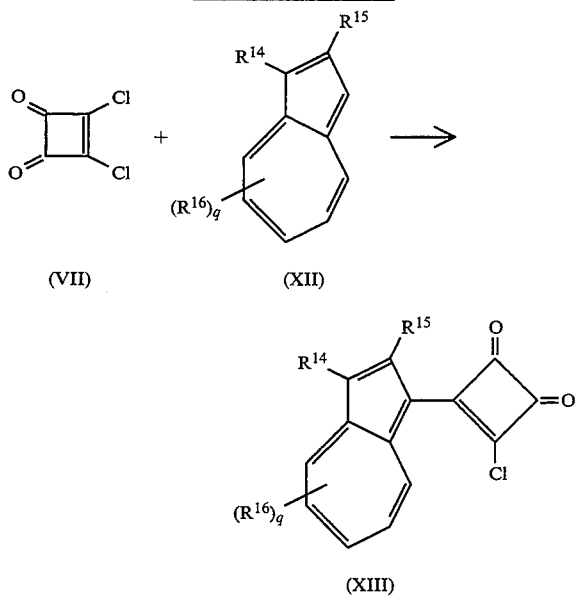

Reaction Scheme (8)

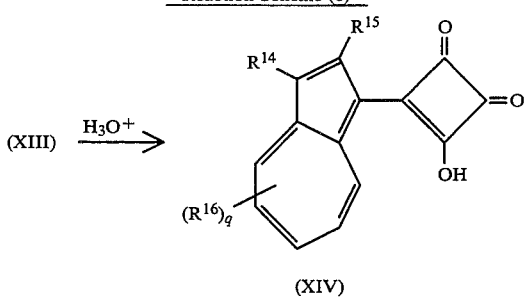

Reaction Scheme (9)

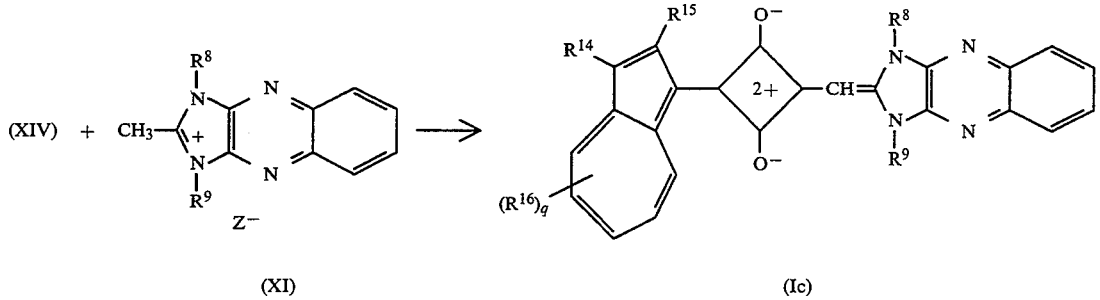

In the Reaction Schemes, $R^8$, $R^9$, $R^{14}$, $R^{15}$, $R^{16}$ and q are the same as defined above, and Z represents chlorine, bromine or iodine atom.

In the reaction (7), a compound (VII) and the equivalent amount of a compound (XII) are reacted at room temperature in a solvent which dissolve these compounds and dose not inhibit the reaction. The reaction is completed in 5 to 60 minutes. As the solvent to be used, there are chloroform, dichloromethane, 1,2-dichlorethane, diethyl ether, tetrahydrofuran, toluene, benzene, dimethylformamide, dimethyl sulfoxide and the like. The solvent is distilled off from the reaction mixture or the product is filtered to give a compound (XIII).

In the reaction (8), the reaction is carried out by heating the compound (XIII) at 90° to 110° C. in a 50 to 90 (wt.) % aqueous solution of acetic acid. The reaction is completed in 1 to 2 hours. The solvent is distilled off to give a compound (XIV).

The reaction (9) is carried out by reacting the compound (XIV) and the equivalent moles of a compound (XI) at 90° to 110° C. in a solvent in the presence of the equivalent moles of a base. The reaction is completed in 1 to 5 hours. As the base to be used, there are the organic bases such as pyridine, quinoline, triethylamine and the like.

As the solvent, an alcoholic solvent having 4 to 6 carbon atoms is used sole or in admixture with benzene or toluene (alcohol is not less than 50%).

After the reaction, a compound (Ic) is isolated by column chromatography.

A squarylium compound (Id) wherein X represents the group (C) and Y represents the group (B) can be prepared by reacting the compound (V) produced by reaction (2) as described before and the imidazoquinoxalinium derivative (XI) produced by reaction (6) as descried before in a solvent in the presence of a base. The reaction is shown in the following Reaction Schemes.

Reaction Scheme (10)

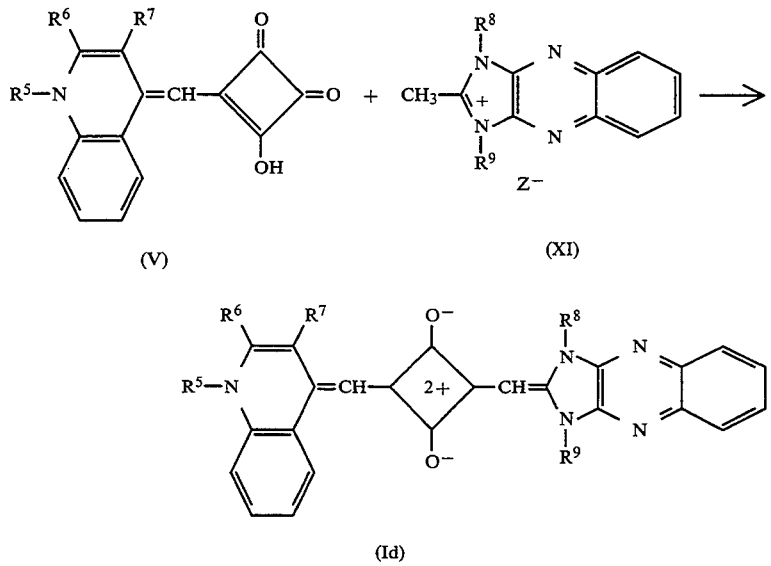

In the Reaction Schemes, $R^5$, $R^6$, $R^7$, $R^8$, $R^9$ and Z are the same as defined above.

The reaction (10) is carried out by reacting the compound (V) and the equivalent moles of a compound (XI) at 90° to 110° C. in the presence of the equivalent moles of a base. The reaction is completed in 1 to 5 hours. As the base to be used, there are the organic bases such as pyridine, quinoline, triethylamine and the like.

As the solvent, an alcoholic solvent having 4 to 5 carbon atoms is used sole or in admixture with benzene or toluene (alcohol is not less than 50%).

After the reaction, the product is isolated by column chromatography to give a compound (Id).

The present invention also provides an optical information recording medium composed of a substrate, a recording layer provided on the base directly or via an under coating layer and, if necessary, a protecting layer further provided thereon characterized in that said recording layer contains the squarylium compound represented by the formula (I).

The recording medium is fundamentally composed of a substrate and a recording layer provided on the substrate, said recording layer comprising the organic pigment of the general formula (I). The recording medium may be provided, if necessary, with an under coating layer between the substrate and the recording layer, or with the protecting layer on the recording layer. Further, one pair of thus obtained recording media may be in the form of air-sandwich structure in which both recording media are sealed with each recording layer inside and via the air between the other substrate. Alternatively, one pair of recording media may be in the form of adherent sandwich (laminated) structure in which both recording media are adhered via a protecting layer.

The present invention further provides an optical information recording medium composed of a substrate, a recording layer provided on the substrate directly or via an under coating layer, and a metallic reflecting layer and a protecting layer further provided on the recording layer in this order, wherein the reflecting layer from the substrate side is not less than 65%, characterized in that the recording layer contains the squarylium compound represented by the general formula (I).

The recording medium is composed of a substrate, a recording layer containing the organic pigment represented by the general formula (I) provided on the substrate, and a metallic reflecting layer and a protecting layer further provided thereon. If necessary, a visible information may be printed on the protecting layer.

The recording medium claimed is intended to be reproduced using a commercially available CD player, it must satisfy with the specification on the previous CD. Therefore, it is necessary that the above reflectance is not less than 65%.

Then, materials for the present optical information recording medium and requisite properties for each layer are explained.

Substrate

The substrate must be transparent for the laser rays to be used only when reproduction is carried out from the substrate side. However, the substrate is not necessarily transparent when reproduction is carried out from the recording layer side. As the material which satisfies with the above requisite properties, there are plastics such as polyester resin, acrylic resin, polyamide resin, polycarbonate resin, polyolefin resin, phenolic resin, epoxy resin and polyimide resin, as well as glasses, ceramics and metals. Optionally, a guide groove and guide pit for tracking and further preformat such as address signal may be formed on the surface of the substrate.

Recording Layer

"The recording layer" used herein refers to a layer in which any optical change is produced by radiation of the laser rays and the information can be recorded utilizing such the change. The recording layer in the present invention is constituted by the above squarylium compound as the main component. The squarylium compound may be used sole or in combination with a pigment such as polymethine pigment, naphthalocyanin, phthalocyanin, squarylium, croconium, pyrylium, naphthoquinone, anthraquinone (indanthrene), xanthene, triphenylmethane, azulene, tetrahydrocoline, phenanthrene and triphenothiazine dye, and metal complex and the like.

In addition, metal or metal compound such as In, Te, Bi, Al, Be, $TeO_2$, SnO, As, Cd may be dispersed, mixed or laminated in the above pigment or dye. Further, polymer material such as ionomer resin, polyamide resin, vinyl resin, natural polymer, silicone, liquid rubber, and silane coupling agent may be dispersed or mixed in the above pigment or dye. For improving the properties, stabilizing agent (for example, transition metal complex), dispersing agent, flame-retandant, lubricant, antistatic agent, surfactant, plasticizer and the like may be contained in the pigment or dye. In particular, for improving the light stability, an aminium, diimonium compound, bisdithio-$\alpha$-diketone metal complex or bisphenyldithiole metal complex which absorbs the light having longer wavelength in comparison with the squarylium compound may be effectively mixed or dispersed therein.

The recording layer can be formed by the conventional means such as vacuum deposition, sputtering, CFD, solution coating and the like. Solution coating can be carried out by dissolving the above dye and the like in an organic solvent and coating the solution according to the conventional method such as spraying, roller coating, dipping, spin-coating and the like. As the organic solvent, there can be used alcohols such as methanol, ethanol, isopropanol and the like, ketones such as acetone, methyl ethyl ketone, cyclohexanone and the like, amides such as N,N-dimethylacetamide, N,N-dimethylformamide and the like, sulfoxides such as dimethyl sulfoxide and the like, ethers such as tetrahydrofuran, dioxane, diethyl ether, ethylene glycol monomethyl ether and the like, esters such as methyl acetate, ethyl acetate and the like, aliphatic halogenated hydrocarbons such as chloroform, methylene chloride, dichloroethane, carbon tetrachloride, trichlorethane and the like, and aromatic compounds such as benzene, xylene, monochlorobenzene, dichlorobenzene and the like. The thickness of the recording layer is 100 Å to 10 $\mu$m, preferably, 200 Å to 1000 Å.

Under Coating Layer

The under coating layer is provided for the purpose of (a) improvement in adhesion properties, (b) barrier to water or gas, (c) improvement in storage stability of recording layer, (d) improvement in reflectance, (e) protection of the substrate from solvent, (f) formation of guide groove, guide pit, preformat and the like. For the purpose (a), there can be used the polymer materials such as inomer resin, polyamide resin, vinyl resin, natural resin, natural polymer, silicone, liquid rubber and the like, as well as silane coupling agent. For the purposes (b) and (c), there can be used the inorganic materials such as $SiO_2$, $MgF_2$, SiO, $TiO_2$, ZnO, TiN, SiN and the like, metal or metalloid such as Zn, Cu, Ni, Cr, Ge, Se, Au, Ag, Al and the like. For the purpose (d), there can be used the metals such as Al, Ag and the like, organic thin layer made of methine dye, xanthene dye and the like having the metallic luster. For the purposes (e) and (f), there can be used ultraviolet curing resin, thermosetting resin, thermoplastic resin and the like. The thickness of the under coating layer is 0.01 to 30 $\mu$m, preferably, 0.05 to 10 $\mu$m.

Protecting Layer and Substrate Surface Hardcoat Layer

Protecting layer or substrate surface hardcoat layer is provided for the purposes of (a) protection of the recording layer (reflecting and absorbing layer) from crack, dust, contamination and the like, (b) improvement in storage stability of recording layer (reflecting and absorbing layer), (c) improvement in reflectance and the like. For these purposes, the above materials described for the under coating layer can be used. In addition, as inorganic materials, SiO, $SiO_2$ and the like can be also used. As organic materials, the thermosoftening or thermomelting resins such as polymethylacrylate resin, polycarbonate resin, epoxy resin, polystyrene resin, polyester resin, vinyl resin, cellulose, aliphatic hydrocarbon resin, aromatic hydrocarbon resin, natural rubber, styrenebutadiene resin, chloroprene rubber, wax, alkyd resin, drying oil, rosin and the like and be used. Most preferably, the ultraviolet curing resins having good productivity are used. The thickness of the protecting layer or substrate surface hardcoat layer is 0.02 to 30 μm, preferably, 0.05 to 10 μm. Stabilizing agent, dispersing agent, flame-retardant, lubricant, antistatic agent, surfactant, plasticizer and the like can be contained in the under coating layer, protecting layer or substrate surface hardcoat layer as in the case of the recording layer.

Metal Reflecting Layer

As the materials for the reflecting layer, the metal, metalloid and the like which, as a simple substance, can give the high reflectance and is not readily corroded. The examples of such the materials are Au, Ag, Cu, Cr, Ni, Al and the like. Preferably, Au and Al are used. These metals and metalloids can e used sole or as an alloy composed of not less than two kinds of them. As a method for forming a membrane, there are vacuum deposition, sputtering and the like. The thickness of the membrane is 50 to 3000 Å, preferably, 100 to 1000 Å.

Spacer

As the materials for the spacer, there are plastics, glasses, ceramics, metals and the like. Preferably, the plastics, for example, resins such as polycarbonate resin, ABS resin, polyolefin resin, polyamide resin, acrylic resin, vinyl chloride resin and the like. Preferably, the same material is used for the inner and outer spacers.

Adhesives

As the adhesive, the ultraviolet curing adhesives having the higher productivity are desirable. For example, in addition to the ultraviolet curing acrylate, epoxy and ene-thiole adhesive, there are thermosetting adhesive, room temperature setting adhesive, hot melt adhesive, solvent-type adhesive, two-part adhesive or pressure sensitive adhesive.

The following Examples and Comparative Examples further illustrate the present invention in detail but are not to be construed to limit the scope thereof.

EXAMPLE 1

Preparation of a compound represented by the formula:

A mixture of 1.98 g of 3,4-diisopropoxy-3-cyclobuten-1,2-dione, 2.99 g of N-ethyllepidinium iodide and 20 ml of isopropanol was stirred at room temperature, and 0.23 g of sodium was added thereto to stir for 4 hours. The insolubles were filtered off, the filtrate was concentrated, and the residue was purified by column chromatography. To this purified material were added 30 ml of acetic acid and 10 ml of water, and the mixture was heated to react at 90° to 100° C. for 1.5 hours. After the reaction was completed, the volatile fraction was concentrated and dried. The dried material was mixed with 0.37 g of 1,3,3-trimethyl-2-methyleneindoline, 21 ml of n-butanol and 21 ml of benzene, and the mixture was heated to reflux for 5 hours. After reflux, the volatile fraction was concentrated, and the residue was purified by column chromatography to give 0.24 g of the titled compound.

Melting point: 260°–263° C. (dec.)

Elementary analysis: Calc. (%): C, 79.59; H, 6.20; N, 6.63. Found (%): C, 79.90; H, 6.15; N, 6.80.

Absorption properties $\lambda_{max}$: 746 nm log ε:5.3 solvent: chloroform

EXAMPLE 2

Preparation of a compound represented by the formula:

0.1 g of the titled compound was prepared according to the same manner as that in Example 1 except that 0.71 g of 1',2'-dimethylspiro[cyclohexane-1,3'-3H-indolium-]iodide and 0.28 g of quinoline were added in place of 1,3,3-trimethyl-2-methyleneindoline.

Melting point: 239°–241° C. (dec.)

Elementary analysis: Calc. (%): C, 80.49; H, 6.54; N, 6.06. Found (%): C, 80.71; H, 6.32; N, 6.28.

Absorption properties $\lambda_{max}$: 752 nm log ε: 5.0 solvent: chloroform

EXAMPLE 3

Preparation of a compound represented by the formula:

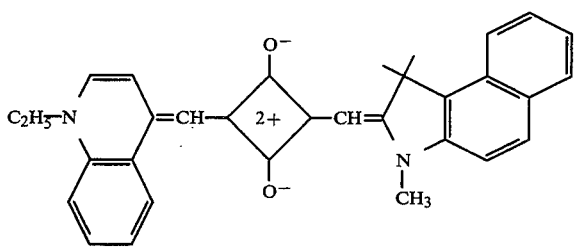

0.17 g of the titled compound was prepared according to the same manner as in Example 1 except that 0.72 g of 1,1,2,3-tetramethyl-1H-benz[e]indolium iodide and 0.28 g of quinoline were added in place of 1,3,3-trimethyl-2-methyleneindoline.

Melting point: 266°–267.6° C. (dec.)

Elementary analysis: Calc. (%): C, 81.33; H, 5.97; N, 5.93. Found (%): C, 81.52; H, 6.06; N, 5.97.

Absorption properties
$\lambda_{max}$: 761 nm
log $\epsilon$: 5.3
solvent: chloroform

EXAMPLE 4

Preparation of a compound represented by the formula:

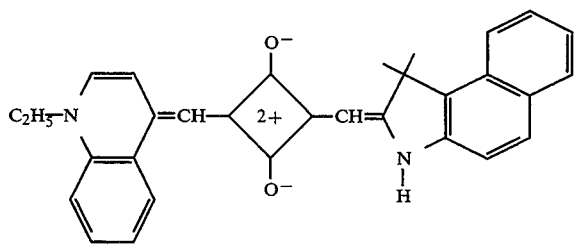

0.01 g of the titled compound was prepared according to the same manner as that in Example 1 except that 0.43 g of 1,1,2-trimethyl-1H-benz[e]indole and 0.27 g of quinoline were added in place of 1,3,3-trimethyl-2-methyleneindoline.

Elementary analysis: Calc. (%): C, 81.20; H, 5.72; N, 6.11. Found (%): C, 81.48; H, 5.63; N, 6.32.

Absorption properties
$\lambda_{max}$: 769 nm
log $\epsilon$: 5.0
solvent: chloroform

EXAMPLE 5

Preparation of a compound represented by the formula:

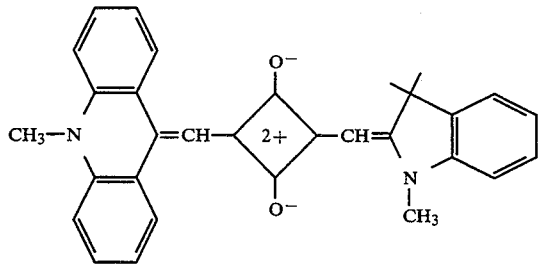

1.61 g of trimethylamine was added to 161 ml of a dichloromethane solution containing 3.5 g of 9,10-dimethylacridinium metalsulfite followed by addition of 7 ml of a dichloromethane solution containing 1.68 g of 3,4-dichloro-3-cyclobuten-1,2-dione, and the mixture was stirred at room temperature for 2 hours. Thereafter, the solvent and volatile fraction were distilled off under reduced pressure, the residue was dissolved in 315 ml of dimethylformamide, the solution was poured into 700 ml of water, the insolubles were filtered, washed with water and dried. 82 ml of acetic acid and 28 ml of water were added thereto, and the mixture was heated to reflux for 2 hours. After the reaction was complete, the solvent and the volatile fraction were concentrated under reduced pressure. Each 52 ml of n-butanol and benzene and 1.18 g of 1,3,3-trimethyl-2-methyleneindoline were added thereto, and the mixture was heated to reflux for 5 hours. Thereafter, the mixture was cooled on ice-water, the precipitates were filtered, washed with butanol to give 1.4 g of the titled compound.

Melting point: 254.5°–257° C. (dec.)

Elementary analysis: Calc. (%): C, 81.20; H, 5.72; N, 6.11. Found (%): C, 81.51; H, 5.62; N, 6.29.

Absorption properties
$\lambda_{max}$: 747 nm
log $\epsilon$: 4.9
solvent: chloroform

EXAMPLE 6

Preparation of a compound represented by the formula:

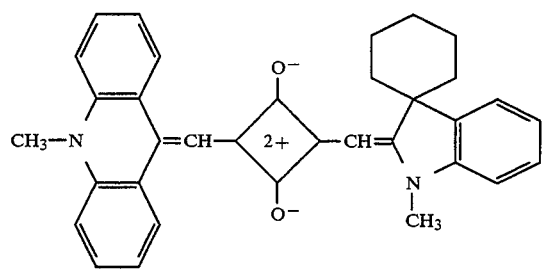

1.06 g of the titled compound was prepared according to the same manner as in Example 5 except that 2.32 g of 1,2-dimethylspiro[cyclohexane-1,3'-3H-indolium]iodide and 0.92 g of quinoline were added in place of 1,3,3-trimethyl-2-methyleneindoline.

Melting point: ≧127° C. (dec.)

Elementary analysis: Calc. (%): C, 81.90; H, 6.06; N, 5.62. Found (%): C, 82.20; H, 5.82; N, 5.47.

Absorption properties
$\lambda_{max}$: 743 nm
log $\epsilon$: 4.9
solvent: chloroform

EXAMPLE 7

Preparation of a compound represented by the formula:

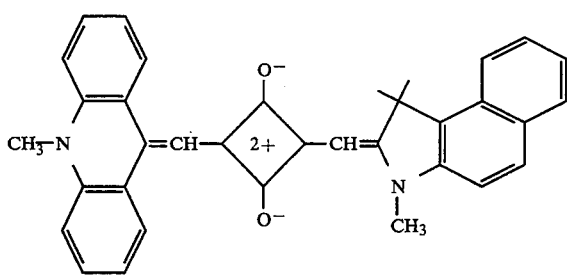

0.29 g of the titled compound was prepared according to the same manner as that in Example 5 except that 2.19 g of 1,1,2,3-tetramethyl-1H-benz[e]indolium iodide and 0.87 g of quinoline were added in place of 1,3,3-trimethyl-2-methyleneindoline.

Melting point: 230.5°–232.5° C. (dec.)

Elementary analysis: Calc. (%): C, 82.65; H, 5.55; N, 5.51. Found (%): C, 82.82; H, 5.72; N, 5.48.

Absorption properties
$\lambda_{max}$: 756 nm
log $\epsilon$: 4.9
solvent: chloroform

EXAMPLE 8

Preparation of a compound represented by the formula:

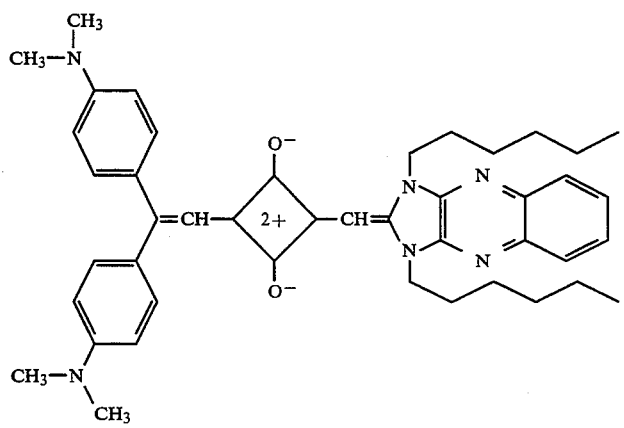

15 ml of dichloromethane was added to 0.3 g of 3,4-dichloro-3-cyclobuten-1,2-dione, and 0.54 g of 1,1-bis(p-dimethylaminophenyl)ethylene was added to stir at room temperature for 1 hour. Dichloromethane was distilled off from the reaction mixture under reduced pressure, and 7.6 ml of acetic acid and 1.9 ml of water were added to the residue to heat at 100° C. for 1 hour. Acetic acid and water were distilled off under reduced pressure, and 20 ml of n-butanol and 20 ml of benzene were added to the residue followed by addition of 1.05 g of 1,3-di-n-hexyl-2-methylimidazo[4,5-b]quinoxalinium tosylate and 0.27 g of quinoline to heat for 2 hours. Thereafter, the mixture was concentrated under reduced pressure, and purified by column chromatography to give 0.45 g of the titled compound.

Melting point: 147° C. (dec.)

Elementary analysis: Calc. (%): C, 75.83; H, 7.52; N, 12.06. Found (%): C, 76.13; H, 7.54; N, 12.26.

Absorption properties
$\lambda_{max}$: 763 nm
log $\epsilon$: 5.0
solvent: chloroform

EXAMPLE 9

Preparation of a compound represented by the formula:

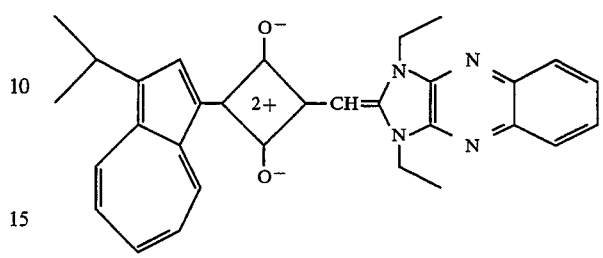

25 ml of dichloromethane was added to 2.27 g of 3,4-dichloro-3-cyclobuten-1,2-dione, a mixture of 2.56 g of 1-isopropylazulene and 25 ml of dichloromethane was added thereto, the mixture was stirred for 1 hour, and dichloromethane was distilled off under reduced pressure. 45 ml of acetic acid and 8 ml of water were added to the residue to heat at 100° C. for 2.5 hours, and acetic acid and water were distilled off under reduced pressure. 50 ml of n-butanol and 50 ml of benzene were added to the residue followed by addition of 4.15 g of 1,3-diethyl-2-methylimidazo[4,5-b]quinoxalinium chloride and 2.0 g of quinoline to heat for 4 hours. Thereafter, the solvent and produced water were distilled off under reduced pressure, and the residue was purified by column chromatography to give 1.4 g of the titled compound.

Melting point: $\geq 300°$ C.

Elementary analysis: Calc. (%): C, 76.21; H, 5.78; N, 11.47. Found (%): C, 76.50; H, 5.62; N, 11.31.

Absorption properties
$\lambda_{max}$: 698 nm
log $\epsilon$: 5.1
solvent: chloroform

EXAMPLE 10

Preparation of a compound represented by the formula:

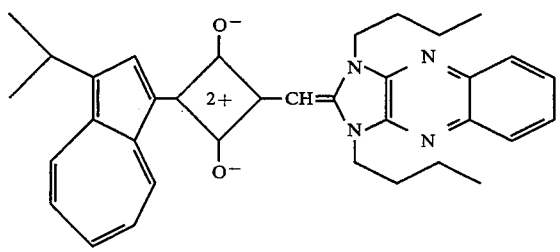

4.4 g of the titled compound was prepared according to the same manner as that in Example 9 except that 7.04 g of 1,3-di-n-butyl-2-methyl[4,5]imidazoquinoxalinium tosylate was used in place of 1,3-diethyl-2-methylimidazo[4,5-b]quinoxalinium chloride.

Melting point: 274.3°–275.9° C. (dec.)

Elementary analysis: Calc. (%): C, 77.18; H, 6.66; N, 10.29. Found (%): C, 77.43; H, 6.55; N, 10.32.

Absorption properties $\lambda_{max}$: 700 nm log $\epsilon$: 5.1 solvent: chloroform

EXAMPLE 11

Preparation of a compound represented by the formula:

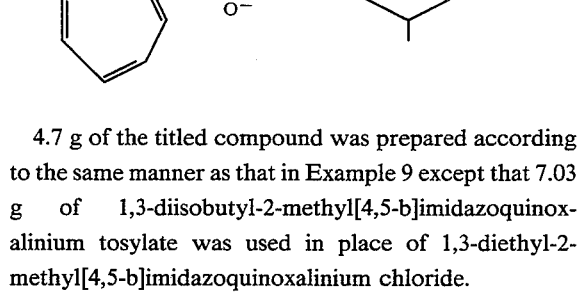

4.7 g of the titled compound was prepared according to the same manner as that in Example 9 except that 7.03 g of 1,3-diisobutyl-2-methyl[4,5-b]imidazoquinoxalinium tosylate was used in place of 1,3-diethyl-2-methyl[4,5-b]imidazoquinoxalinium chloride.

Melting point: 292.5°–295° C. (dec.)

Elementary analysis: Calc. (%): C, 77.18; H, 6.66; N, 10.29. Found (%): C, 77.47; H, 6.38; N, 10.17.

Absorption properties $\lambda_{max}$: 701 nm log $\epsilon$: 5.1 solvent: chloroform

EXAMPLE 12

Preparation of a compound represented by the formula:

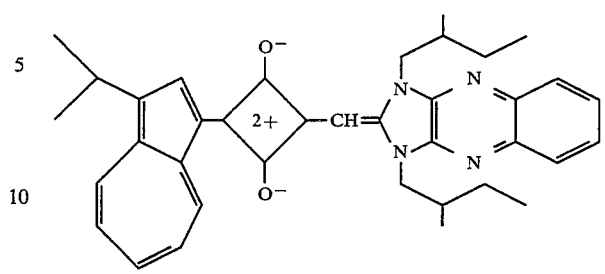

2.8 g of the titled compound was prepared according to the same manner as that in Example 9 except that 7.40 g of 1,3-di-sec-amyl-2-methylimidazo[4,5-b]quinoxalinium tosylate was used in place of 1,3-diethyl-2-methylimidazo[4,5-b]quinoxalinium chloride.

Melting point 244.6°–244.7° C.

Elementary analysis: Calc. (%): C, 77.59; H, 7.04; N, 9.78. Found (%): C, 77.88; H, 7.13; N, 9.62.

Absorption properties $\lambda_{max}$: 700 nm log $\epsilon$: 5.0 solvent: chloroform

EXAMPLE 13

Preparation of a compound represented by the formula:

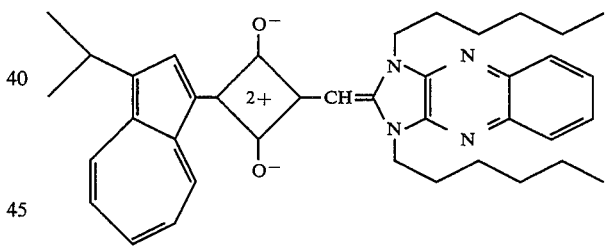

4.9 g of the titled compound was prepared according to the same manner as that in Example 9 except that 7.93 g of 1,3-di-n-hexyl-2-methylimidazo[4,5-b]quinoxalinium tosylate was used in place of 1,3-diethyl-2-methyl[4,5-b]imidazoquinoxalinium chloride.

Melting point: 234.7°–236° C.

Elementary analysis: Calc. (%): C, 77.97; H, 7.38; N, 9.33. Found (%): C, 78.23; H, 7.41; N, 9.56.

Absorption properties $\lambda_{max}$: 700 nm log $\epsilon$: 5.2 solvent: chloroform

EXAMPLE 14

Preparation of a compound represented by the formula:

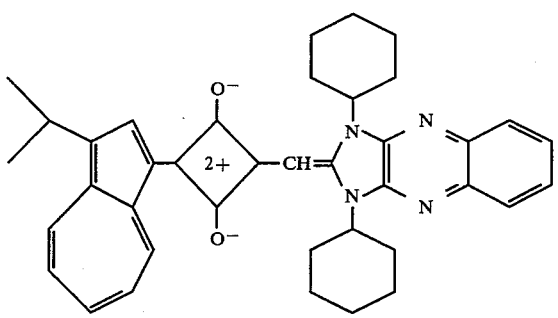

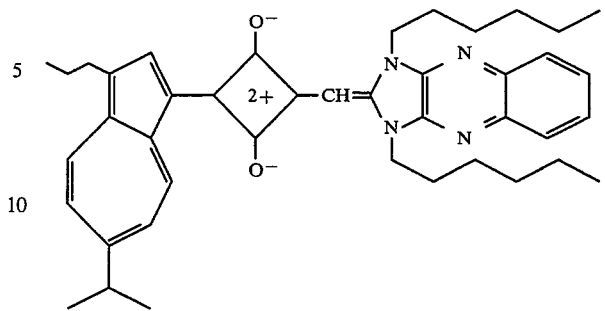

5.2 g of the titled compound was prepared according to the same manner as that in Example 9 except that 7.85 g of 1,3-dicyclohexyl-2-methylimidazo[4,5-b]quinoxalinium tosylate was used in place of 1,3-diethyl-2-methylimidazo[4,5-b]quinoxalinium chloride.

Melting point: 267.2°–269° C.

Elementary analysis: Calc. (%): C, 78.49; H, 6.76; N, 9.39. Found (%): C, 78.83; H, 6.92; N, 9.36.

Absorption properties $\lambda_{max}$: 691 nm log $\epsilon$: 5.1 solvent: chloroform

EXAMPLE 15

Preparation of a compound represented by the formula:

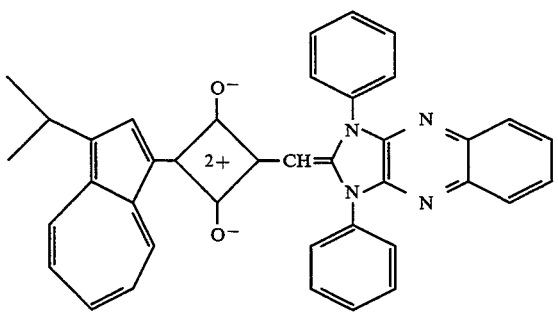

0.83 g of the titled compound was prepared according to the same manner as that in Example 9 except that 7.71 g of 1,3-diphenyl-2-methylimidazo[4,5-b]quinoxalinium tosylate was used in place of 1,3-diethyl-2-methylimidazo[4,5-b]quinoxalinium chloride.

Melting point: 103° C. (dec.)

Elementary analysis: Calc. (%): C, 80.12; H, 4.83; N, 9.58. Found (%): C, 80.42; H, 4.76; N, 9.33.

Absorption properties $\lambda_{max}$: 720 nm log $\epsilon$: 5.0 solvent: chloroform

EXAMPLE 16

Preparation of a compound represented by the formula:

2.05 g of the titled compound was prepared according to the same manner as that in Example 9 except that 3.19 g of 1-n-propyl-6-isopropylazulene was used in place of 1-isopropylazulene, and 7.87 g of 1,3-di-n-hexyl-2-methylimidazo[4,5-b]quinoxalinium tosylate was used in place of 1,3-diethyl-2-methylimidazo[4,5-b]quinoxalinium chloride.

Melting point: 230° C.

Elementary analysis: Calc. (%): C, 78.47; H, 7.84; N, 8.72. Found (%): C, 78.70; H, 7.62; N, 8.98.

Absorption properties $\lambda_{max}$: 719 nm log $\epsilon$: 5.2 solvent: chloroform

EXAMPLE 17

Preparation of a compound represented by the formula:

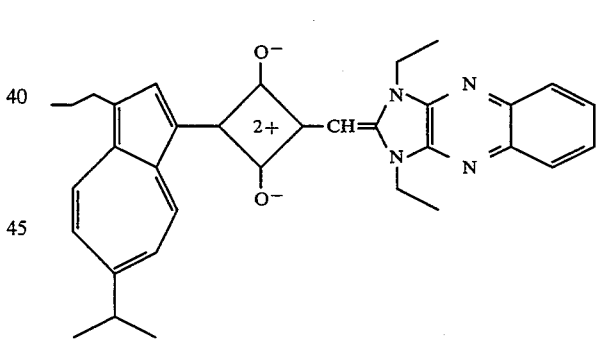

2.56 of the titled compound was prepared according to the same manner as that in Example 16 except that 4.15 g of 1,3-diethyl-2-methylimidazo[4,5-b]quinoxalinium chloride was used in place of 1,3-di-n-hexyl-2-methylimidazo[4,5-b]quinoxalinium tosylate.

Melting point: 274.2°–275.5° C.

Elementary analysis: Calc. (%): C, 76.95; H, 6.46; N, 10.56. Found (%): C, 77.32; H, 6.29; N, 10.74.

Absorption properties $\lambda_{max}$: 719 nm log $\epsilon$: 5.2 solvent: chloroform

EXAMPLE 18

Preparation of a compound represented by the formula:

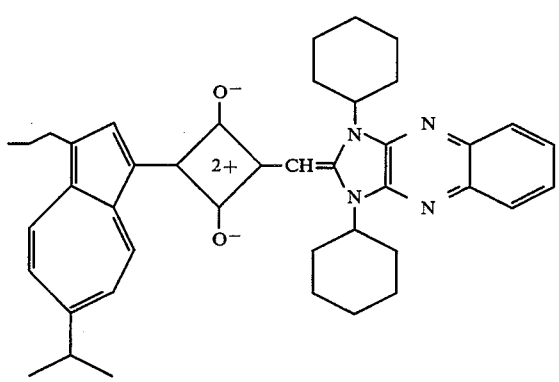

4.1 g of the titled compound was prepared according to the same manner as that in Example 16 except that 7.81 g of 1,3-dicyclohexyl-2-methylimidazo[4,5-b]quinoxalinium tosylate was used in place of 1,3-di-n-hexyl-2-methylimidazo[4,5-b]quinoxalinium tosylate.

Melting point: 240.6°–244.8° C.
Elementary analysis: Calc. (%): C, 78.96; H, 7.26; N, 8.77. Found (%): C, 78.25; H, 7.33; N, 8.92.
Absorption properties
$\lambda_{max}$: 699 nm
log $\epsilon$: 5.1
solvent: chloroform

EXAMPLE 19

Preparation of a compound represented by the formula:

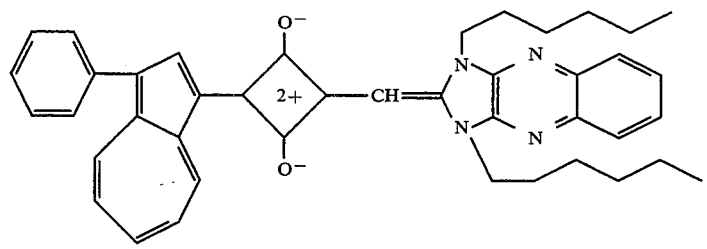

1.36 g of the titled compound was prepared according to the same manner as that in Example 13 except that 3.06 g of 1-phenylazulene was used in place of 1-isopropylazulene.

Melting point: 205° C. (dec.)
Elementary analysis: Calc. (%): C, 79.46; H, 6.67; N, 8.83. Found (%): C, 79.53; H, 6.51; N, 8.72.
Absorption properties
$\lambda_{max}$: 694 nm
log $\epsilon$: 5.0
solvent: chloroform

EXAMPLE 20

Preparation of a compound represented by the formula:

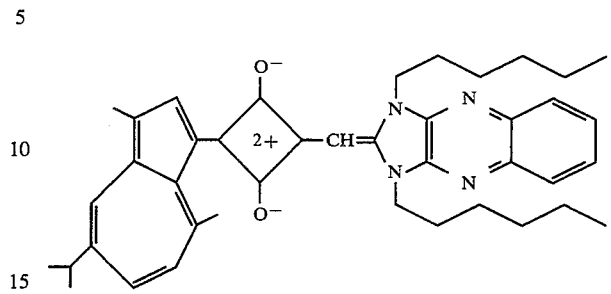

3.07 g of the titled compound was prepared according to the same manner as that in Example 13 except that 3 g of guaiazulene was used in place of 1-isopropylazulene.

Melting point: 174.5°–176.1° C.
Elementary analysis: Calc. (%): C, 78.31; H, 7.69; N, 8.91. Found (%): C, 78.54; H, 7.82; N, 9.06.
Absorption properties
$\lambda_{max}$: 736 nm
log $\epsilon$: 5.0
solvent: chloroform

EXAMPLE 21

Preparation of a compound represented by the formula:

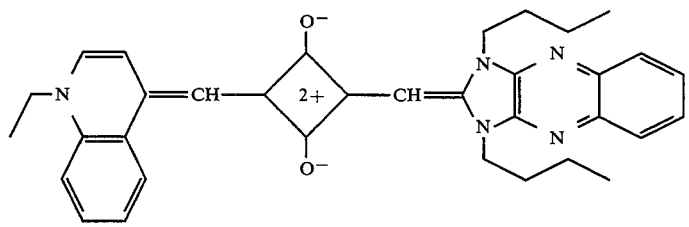

A mixture of 1.98 g of 3,4-diisopropoxy-3-cyclobuten-1,2-dione, 2.99 g of N-ethyllepidinium iodide and 20 ml of isopropanol were stirred at room temperature, and 0.23 g of sodium was added thereto to stir for 4 hours. Thereafter, the insolubles were filtered off, the filtrate was concentrated, and the residue was purified by column chromatography. To this purified material were added 30 ml of acetic acid and 10 ml of water, and the mixture was heated to react at 90° to 100° C. for 1.5 hours. After the reaction was complete, the volatile material was concentrated and dried. Thereafter, the dried material was mixed with 13 ml of n-butanol followed by with 0.92 g of 1,3-din-butyl-2- methylimidazo[4,5-b]quinoxalinium chloride and 0.27 g of quinoline, and the mixture was heated to reflux for 4 hours. The solvent and produced water were distilled off under reduced pressure, and the residue was purified by column chromatography to give 0.31 g of the titled compound.

Melting point: 237°–238° C. (dec.)

Elementary analysis: Calc. (%): C, 74.84; H, 6.47; N, 12.83. Found (%): C, 75.13; H, 6.52; N, 12.94. Absorption properties
$\lambda_{max}$: 784 nm
log $\epsilon$: 5.4
solvent: chloroform

EXAMPLE 22

Spiral guide groove, 1.6 μm in pitch, 2000 Å in depth, 0.4 μm in half value width, was formed on a polymethylmethacrylate (PMMA) circular disc having the thickness of 1.2 mm and the diameter of 130 mm, via acrylic photopolymer having the thickness of 50 μm formed on the PMMA disc. A solution of 1,2-dichloroethane containing 0.8 wt % of the compound obtained in Example 1 was spin-coated on the above substrate as the recording material, and dried to give a recording medium provided with a recording layer having the thickness of about 800 Å.

The spectral chart where the parallel rays are past through the substrate of the smooth part of this recording medium is shown in FIG. 1. It is understood from FIG. 1 that this recording medium shows the high reflectance in the wavelength range (780–830 nm) of semiconductor laser rays which are currently used for the optical disc.

Then, in order to investigate the recording properties of the above recording medium, the writing was carried out through the substrate plane of the above recording medium under the conditions of the recording frequency of 5 MHz, the linear velocity of 2.1 m/sec and the recording power of 3 mW using the semiconductor laser rays having the beam diameter of 1.6 μm and the wavelength of 790 nm, and the reflected rays by the reproducing rays having the light intensity of 0.2 mW/cm$^2$ were detected using the same semiconductor laser rays, the spectral analysis was carried out (Scanning Filter 30 KHz) and the C/N ratio (initial value) was measured. In addition, the reflectance (initial value) was measured at the parallel rays having the wavelength of 790 nm.

Further, in order to evaluate the stability of the above recording medium to the reproducing rays, the reproduction deterioration-accelerated test was carried out as follows: the recording medium was left for 10 hours under 54000 lux tungsten radiation and, thereafter, the reflectance and C/N ratio were measured as described above. The results are shown in Table 1.

Further, in order to evaluate the storage stability of the above recording medium, the storage stability-accelerated test was carried out as follows: the recording medium was left at 60° C. for 800 hours under 90% relative humidity, and then the reflectance and C/N ratio were measured as described above. The results are shown in Table 1.

EXAMPLES 23 AND 24

Figure 2:
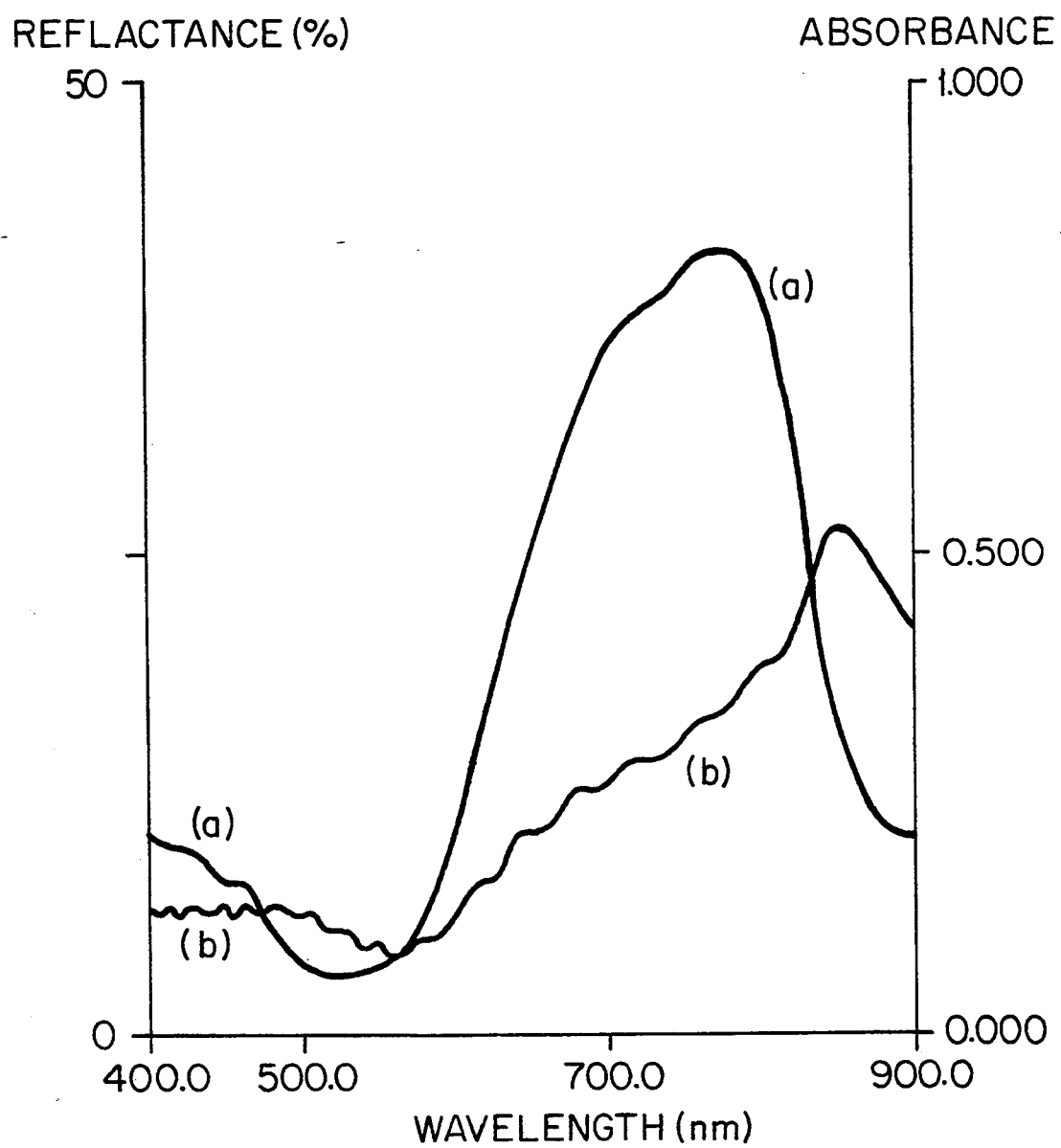
FIG. 2 is a chart showing the spectral properties of the recording medium obtained in Example 23 where the parallel rays are past through the base of the smooth part. (a) shows the absorption spectrum of the recording medium and (b) shows the reflection spectrum where the measuring was carried out through the base of the recording medium.
Figure 3:
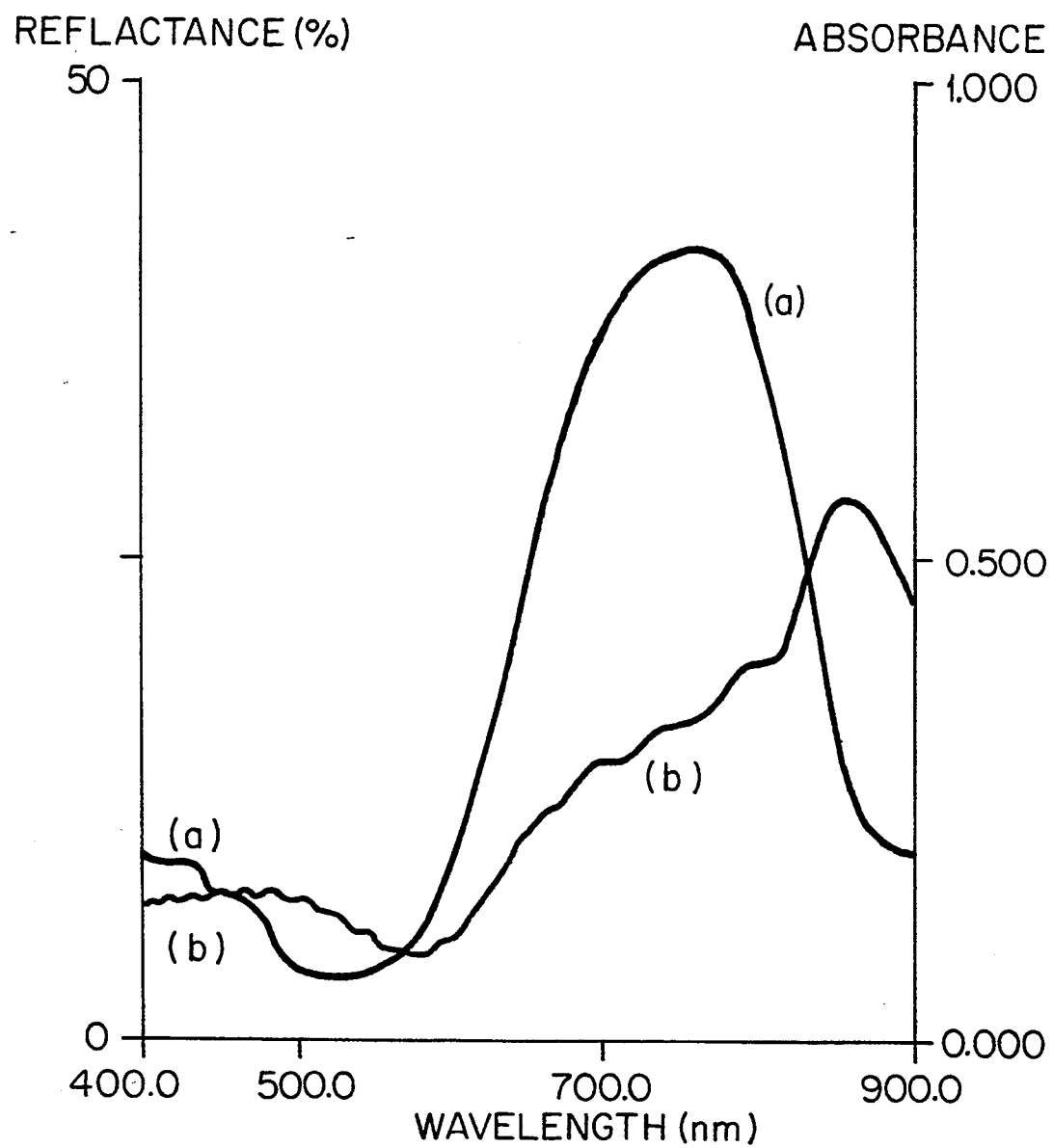
FIG. 3 is a chart showing the spectral properties of the recording medium obtained in Example 24 where the parallel rays are past through the base of the smooth part. (a) shows the absorption spectrum of the recording medium and (b) shows the reflection spectrum where the measuring was carried out through the base of the recording medium.

The corresponding recording medium was obtained according to the same manner as that in Example 22 except that a compound obtained in Example 1 to 2 was used, respectively. The recording properties of these recording media were tested according to the same manner as that in Example 22. The obtained spectral charts are shown in FIGS. 2 and 3 and the recording properties are shown in Table 1.

EXAMPLE 25

A recording medium was obtained according to the same manner as that in Example 22 except that a mixture (weight ratio=85/15) of a compound obtained Example 1 and a dithiole-nickel complex salt compound represented by the formula below was used as a recording material. And the recording properties of this recording medium were measured according to the same manner as that in Example 22. The results are shown in Table 1.

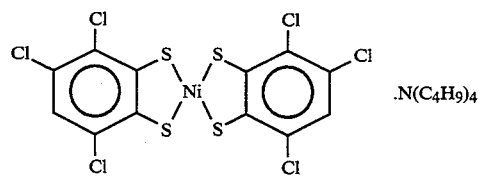

EXAMPLE 26

A recording medium was obtained according to the same manner as that in Example 22 except that a mixture (weight ratio=85/15) of a compound obtained in Example 1 and an aminium compound represented by the formula below was used as a recording material. And the recording properties of this recording medium were measured according to the same manner as that in Example 22. The results are shown in Table 1.

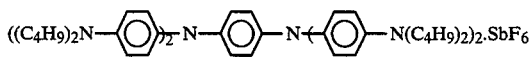

EXAMPLE 27

An injection molded polycarbonate circular disc having the thickness of 1.2 mm and the diameter of 130 mm was prepared using a stamper having the same transcribable groove shape as that in Example 22. A mixed methanol/1,2-dichoroethane/butanol (weight ratio=8/1.5/0.5) solution containing 1 wt % of the compound obtained in Example 3 was spin-coated on the circular disc to give a recording medium.

Figure 4:
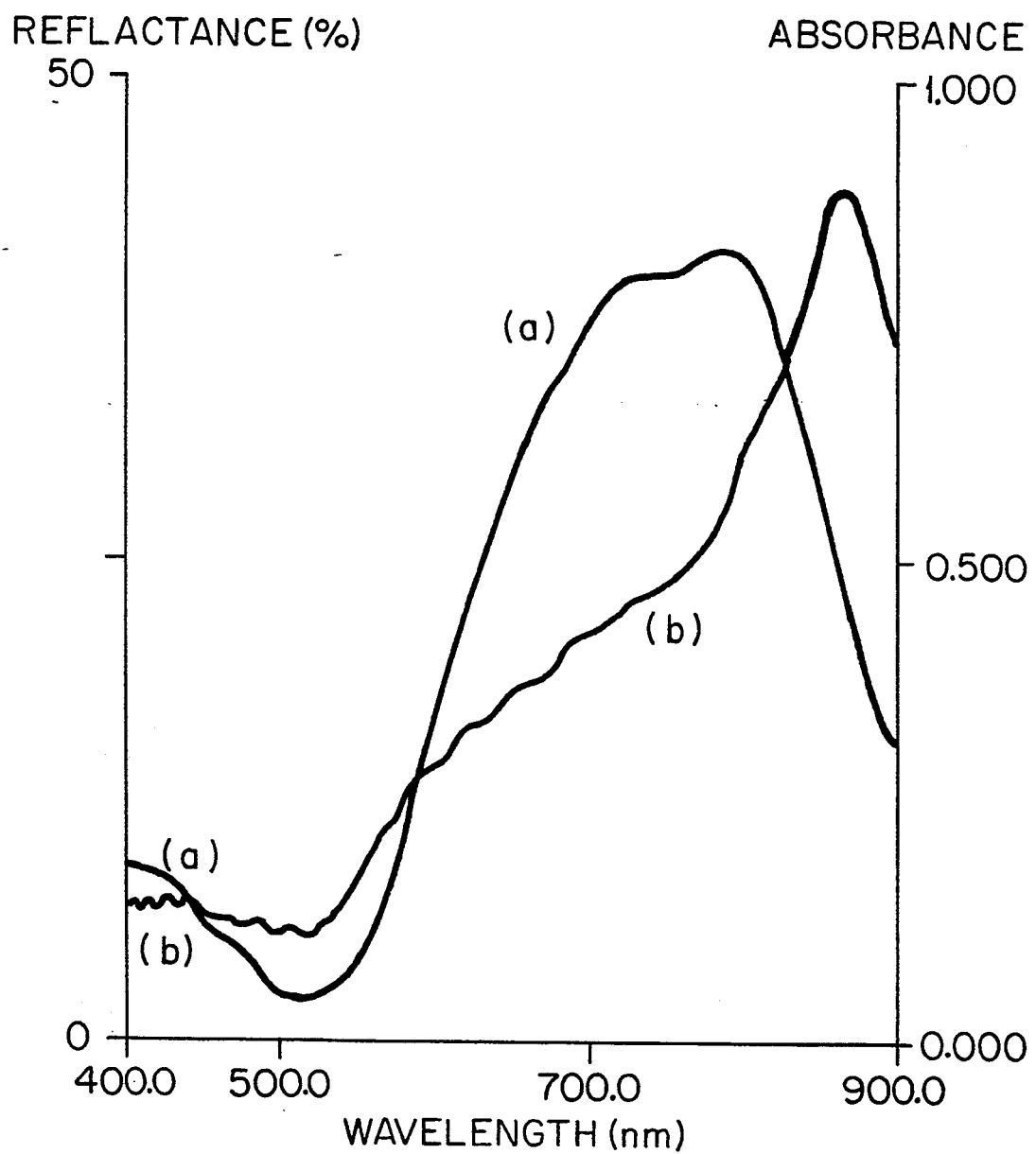
FIG. 4 is a chart showing the spectral properties of the recording medium obtained in Example 27 where the parallel rays are past through the base of the smooth part. (a) shows the absorption spectrum of the recording medium and (b) shows the reflection spectrum where the measuring was carried out through the base of the recording medium.

The spectral properties and the recording properties were measured according to the same manner as that in Example 22 and the results are shown in FIG. 4 and Table 1.

EXAMPLE 28

A recording medium was obtained according to the same manner as that in Example 22 except that a substrate formed by coating a 25% butanol solution of COLCOAT N-103X (manufactured by COLCOAT K.K.) on the same substrate as that in Example 27 and drying at 60° C. for 2 hours was used. The recording properties of this recording medium were measured according to the same manner as that in Example 22. The results are shown in Table 1.

EXAMPLE 29

Figure 5:
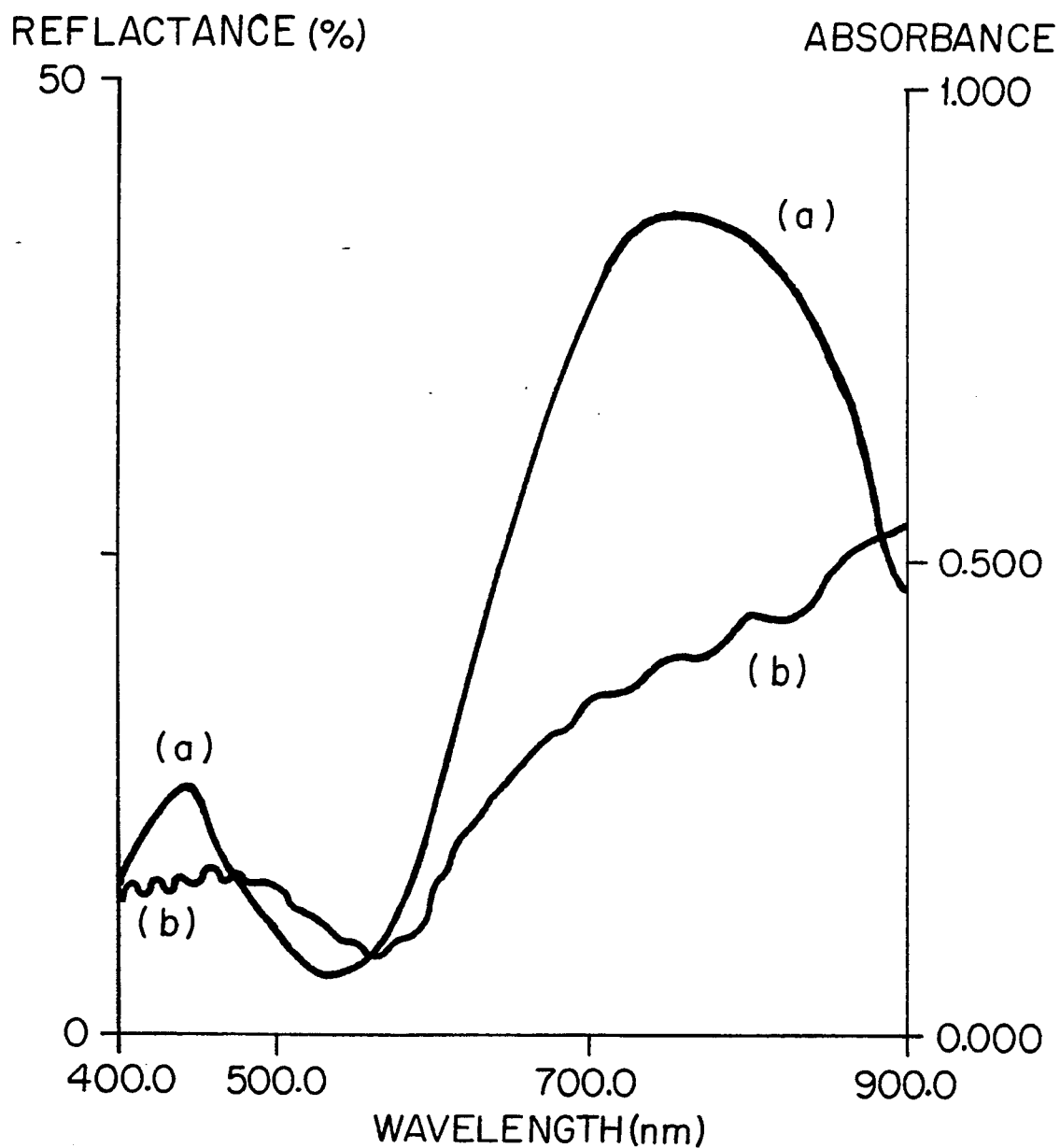
FIG. 5 is a chart showing the spectral properties of the recording medium obtained in Example 29 where the parallel rays are past through the base of the smooth part. (a) shows the absorption spectrum of the recording medium and (b) shows the reflection spectrum where the measuring was carried out through the base of the recording medium.

A recording medium was obtained according to the same manner as that in Example 22 except that the compound obtained in Example 6 was used in place of the compound obtained in Example 1. The recording properties were measured according to the same manner as that in Example 22. The spectral chart is shown in FIG. 5 and the recording properties are shown in Table 1.

Figure 8:
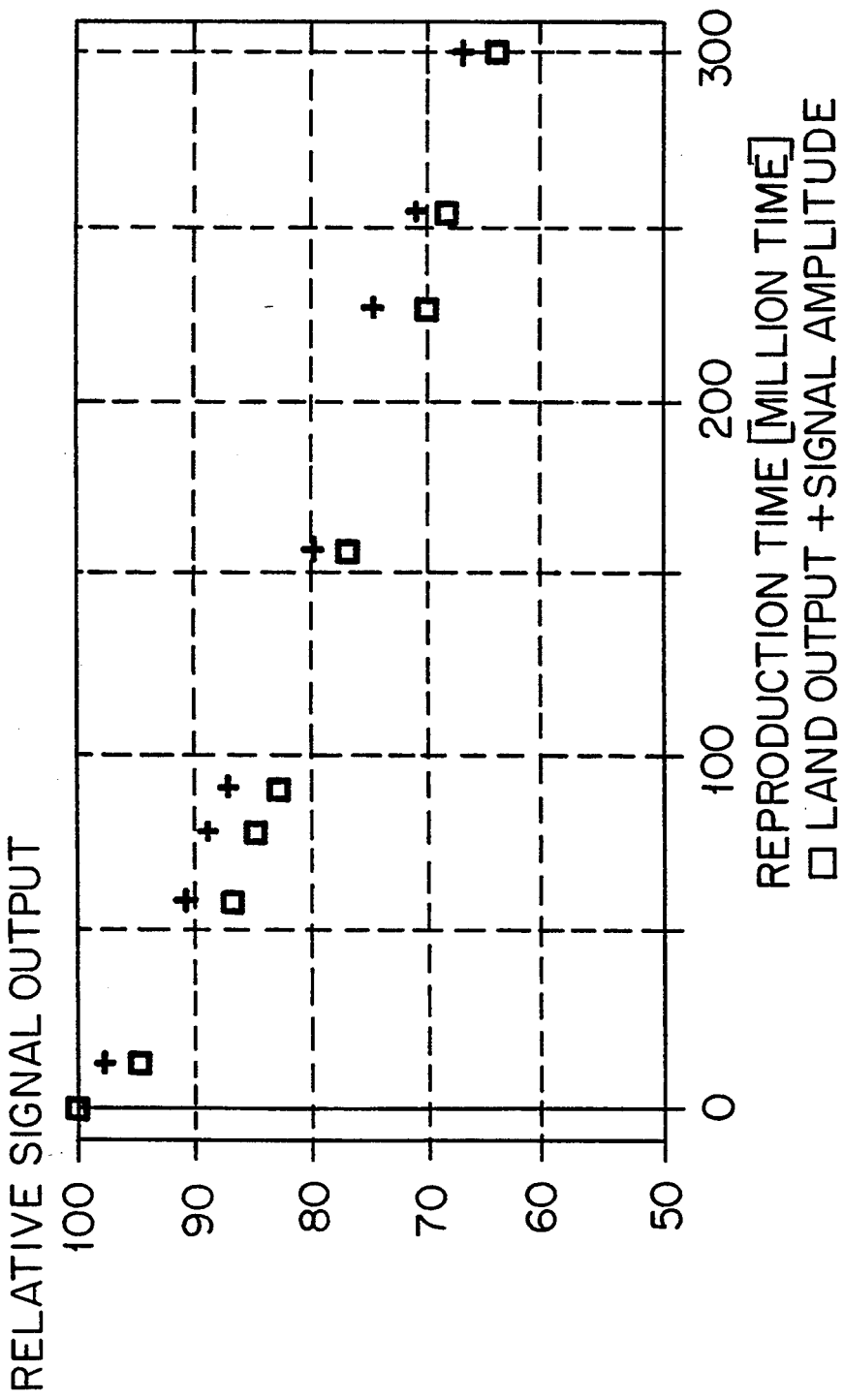
FIG. 8 is a graph showing the relationship between reproduction times and relative signal change in the recording medium obtained in Example 29 when the same track is reproduced 3 million times using the reproducing rays having the light intensity of 0.25 mW/cm$^2$ and the change in the reflectance thereof and signal amplitude is measured as the relative signal change.

In order to evaluate the stability of the above recording medium to the reproducing rays, the same track was reproduced 3 million times using the reproducing rays having the light intensity of 25 mW/cm², and the change in the reflectance and signal amplitude was determined as the relative signal change. The results are shown in FIG. 8.

EXAMPLE 30

Figure 6:
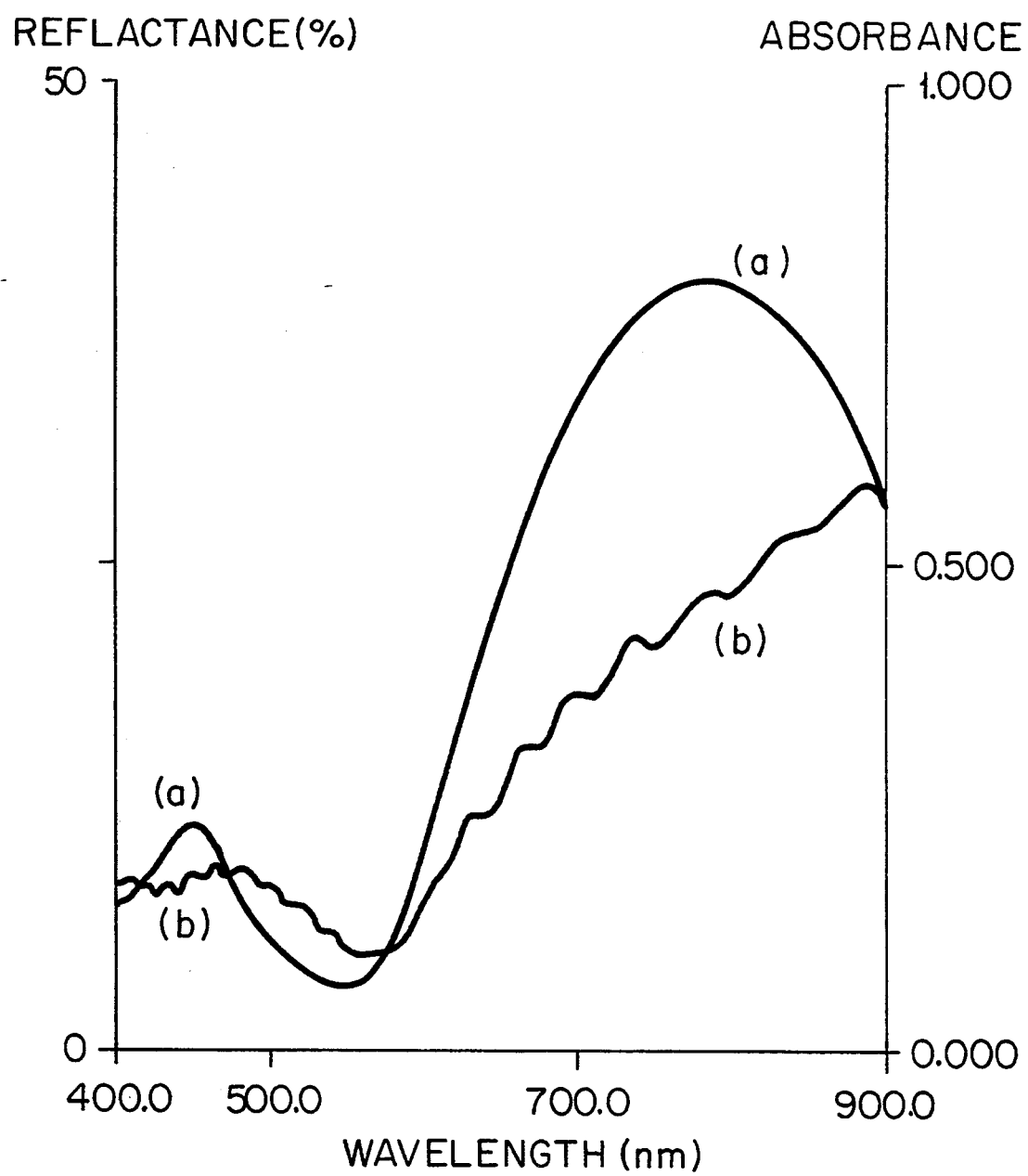
FIG. 6 is a chart showing the spectral properties of the recording medium obtained in Example 30 where the parallel rays are past through the base of the smooth part. (a) shows the absorption spectrum of the recording medium and (b) shows the reflection spectrum where the measuring was carried out through the base of the recording medium.

A recording medium was obtained according to the same manner as that in Example 22 except that the compound obtained in Example 7 was used in place of the compound obtained in Example 1. The recording properties were measured according to the same manner as that in Example 22. The spectral chart is shown in FIG. 6 and the recording properties are shown in Table 1.

EXAMPLE 31

A recording medium was obtained according to the same manner as that in Example 25 except that the compound obtained in Example 6 was used in place of the compound obtained in Example 1. The recording properties were measured according to the same manner as that in Example 22. The results are shown in Table 1.

EXAMPLE 32

A recording medium was obtained according to the same manner as that in Example 26 except that the compound obtained in Example 6 was used in place of the compound obtained in Example 1. The recording properties were measured according to the same manner as that in Example 22. The results are shown in Table 1.

EXAMPLE 33

An injection molded polycarbonate circular disc having the thickness of 1.2 mm and the diameter of 130 mm was prepared using a stamper having the same transcribable groove shape as that in Example 22. A 1,1,2-trifluoroethanol solution containing 1 wt % of the compound obtained in Example 5 was spin-coated on the circular disc to give a recording medium.

Figure 7:
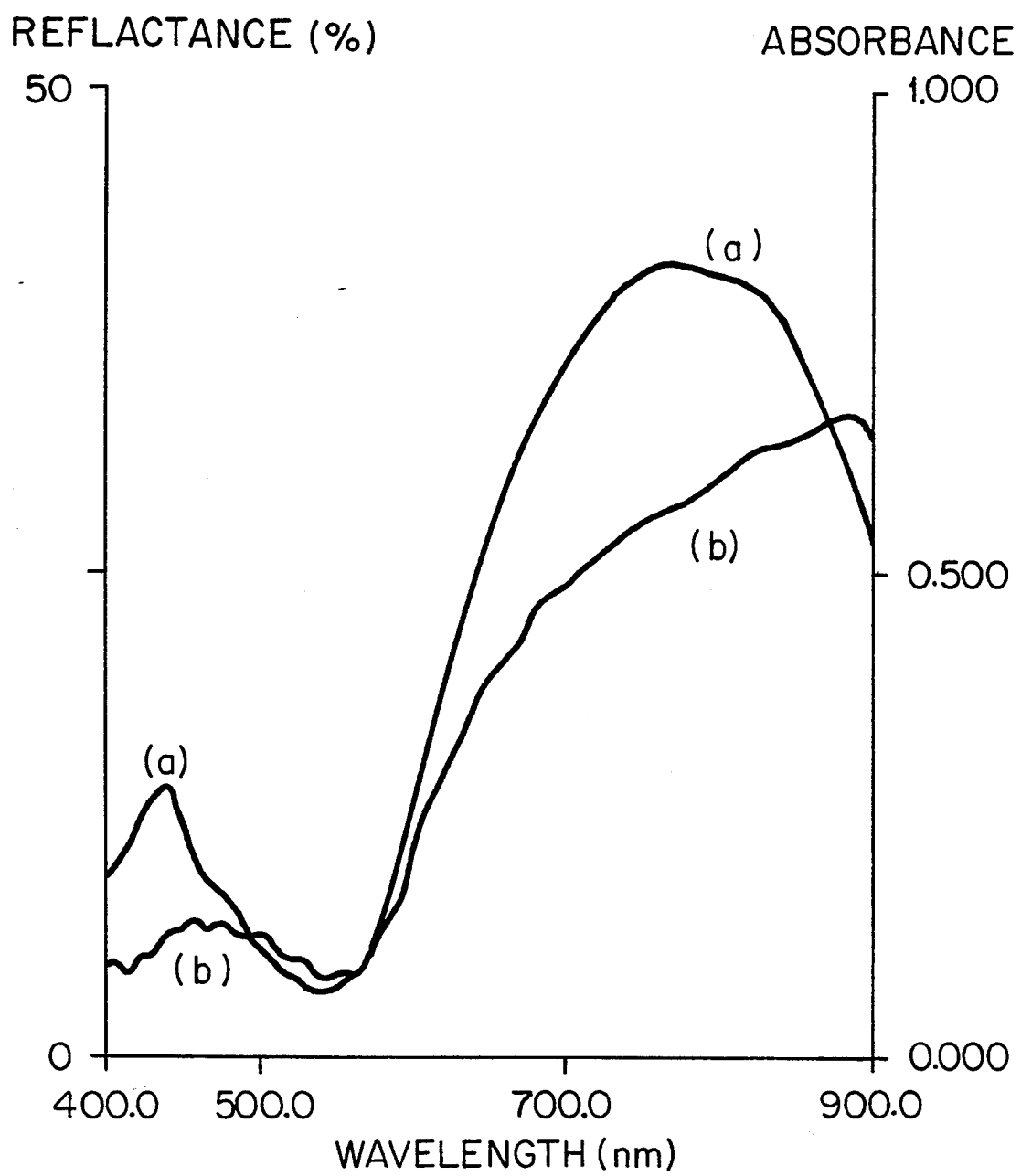
FIG. 7 is a chart showing the spectral properties of the recording medium obtained in Example 33 where the parallel rays are past through the base of the smooth part. (a) shows the absorption spectrum of the recording medium and (b) shows the reflection spectrum where the measuring was carried out through the base of the recording medium.

The spectral properties and recording properties were measured according to the same manner as that in Example 22. The spectral chart is shown in FIG. 7 and the recording properties are shown in Table 1.

EXAMPLE 34

A recording medium was obtained according to the same manner as that in Example 22 except that a mixture (weight ratio=1/1) of the compound obtained in Example 6 and a cyanin compound represented by the formula below was used in place of the compound obtained in Example 1. The recording properties were measured according to the same manner as that in Example 22. The results are shown in Table 1.

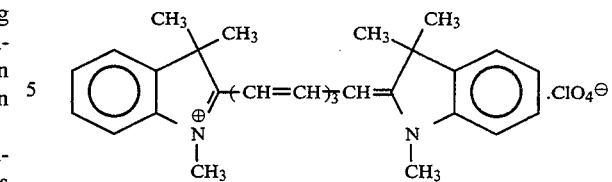

EXAMPLE 35

A recording medium was obtained according to the same manner as that in Example 22 except that a substrate formed by coating a 25% butanol solution of COLCOAT N-103X (manufactured by COLCOAT K.K.) on the same substrate as that in Example 33 and drying at 60° C. for 2 hours was used. The recording properties of this recording medium were measured according to the same manner as that in Example 22. The results are shown in Table 1.

EXAMPLE 36

Figure 9:
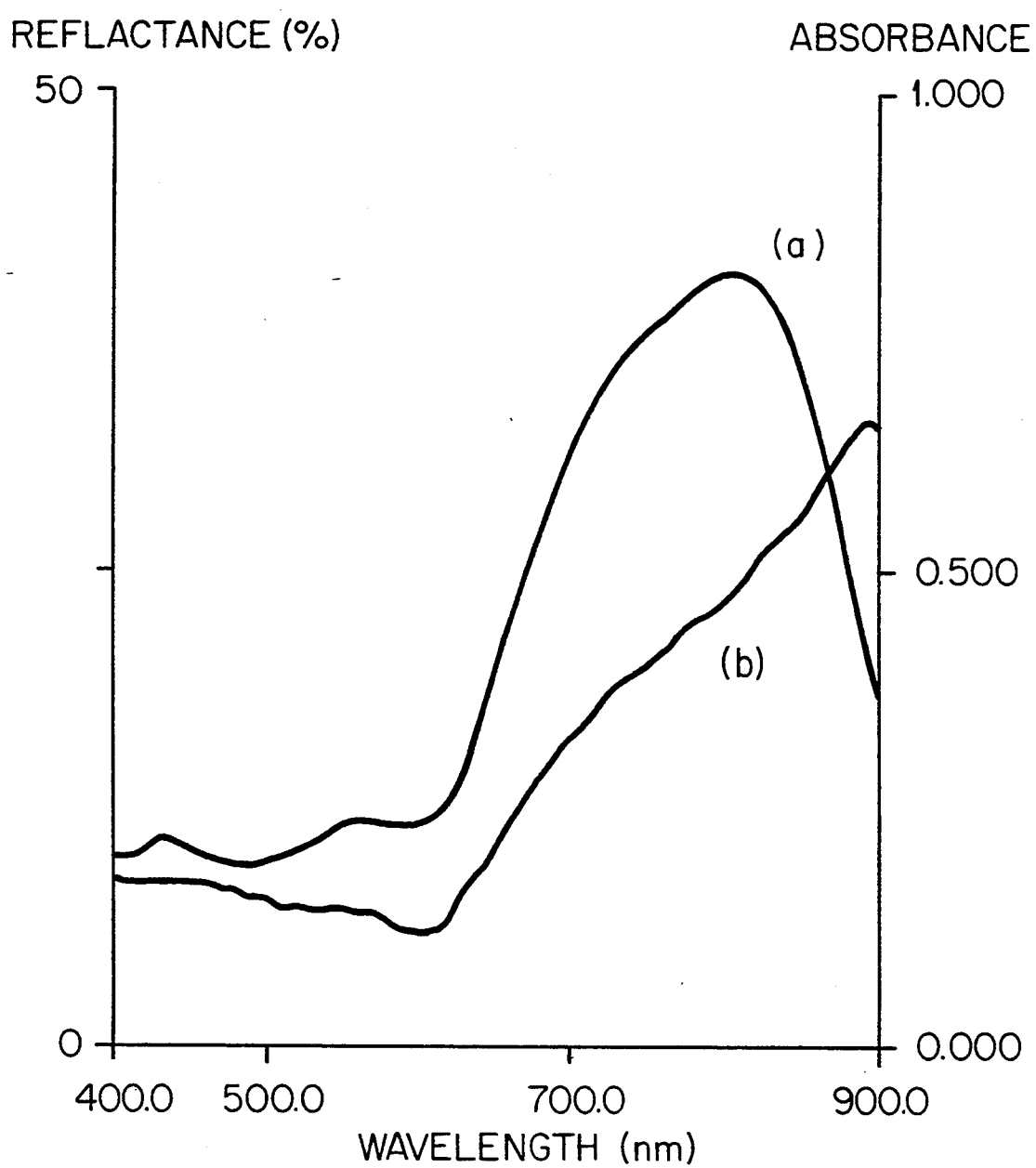
FIG. 9 is a chart showing the spectral properties of the recording medium obtained in Example 36 where the parallel rays are past through the base of the smooth part. (a) shows the absorption spectrum of the recording medium and (b) shows the reflection spectrum where the measuring was carried out through the base of the recording medium.

A recording medium was obtained according to the same manner as that in Example 22 except that a compound obtained in Example 8 was used. The recording properties of this recording medium were measured according to the same manner as that in Example 22.

the obtained spectral chart is shown in FIG. 9 and the recording properties are shown in Table 1.

EXAMPLE 37

A recording medium was obtained according to the same manner as that in Example 25 except that a compound obtained in Example 8 was used in place of the compound obtained in Example 1. And the recording properties of this recording medium were measured according to the same manner as that in Example 22. The results are shown in Table 1.

EXAMPLE 38

A recording medium was obtained according to the same manner as that in Example 26 except that a compound obtained in Example 8 was used in place of the compound obtained in Example 1. And the recording properties of this recording medium were measured according to the same manner as that in Example 22. The results are shown in Table 1.

EXAMPLE 39

A recording medium was obtained according to the same manner as that in Example 27 except that the compound obtained in Example 8 was used in place of the compound in Example 3. The recording properties were measured according to the same manner as that in Example 22 and the results are shown in Table 1.

EXAMPLE 40

A recording medium was obtained according to the same manner as that in Example 22 except that a substrate formed by coating a 25% butanol solution of COLCOAT N-103X (manufactured by COLCOAT K.K.) on the same substrate as that in Example 36 and drying at 60° C. for 2 hours was used. The recording properties of this recording medium were measured according to the same manner as that in Example 22. The results are shown in Table 1.

EXAMPLE 41

Figure 10:
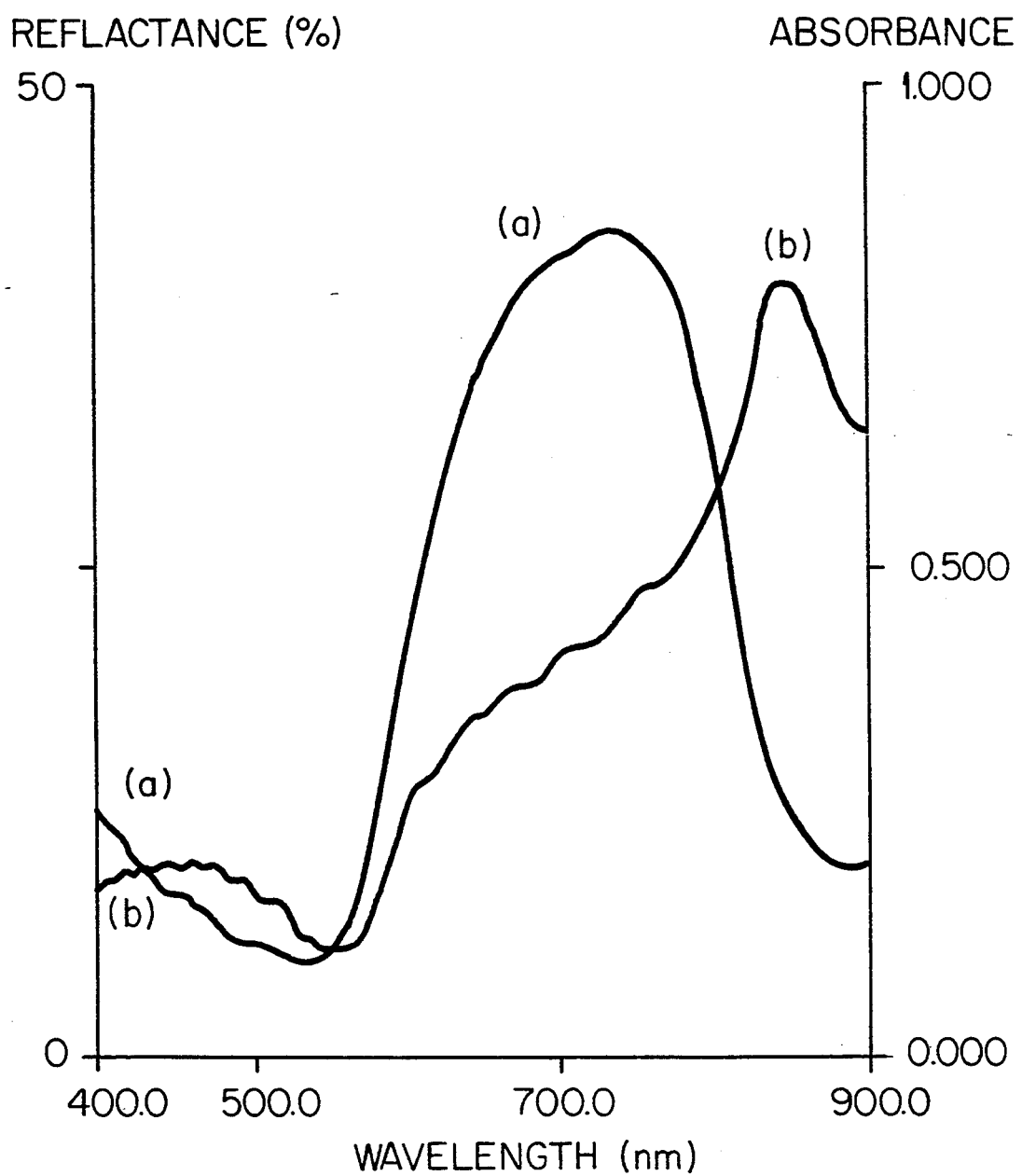
FIG. 10 is a chart showing the spectral properties of the recording medium obtained in Example 41 where the parallel rays are past through the base of the smooth part. (a) shows the absorption spectrum of the recording medium and (b) shows the reflection spectrum where the measuring was carried out through the base of the recording medium.

A recording medium was obtained according to the same manner as that in Example 22 except that the compound obtained in Example 15 was used in place of the compound obtained in Example 1. The spectral properties and recording properties were measured according to the same manner as that in Example 22. The spectral chart is shown in FIG. 10 and the recording properties are shown in Table 1.

Figure 11:
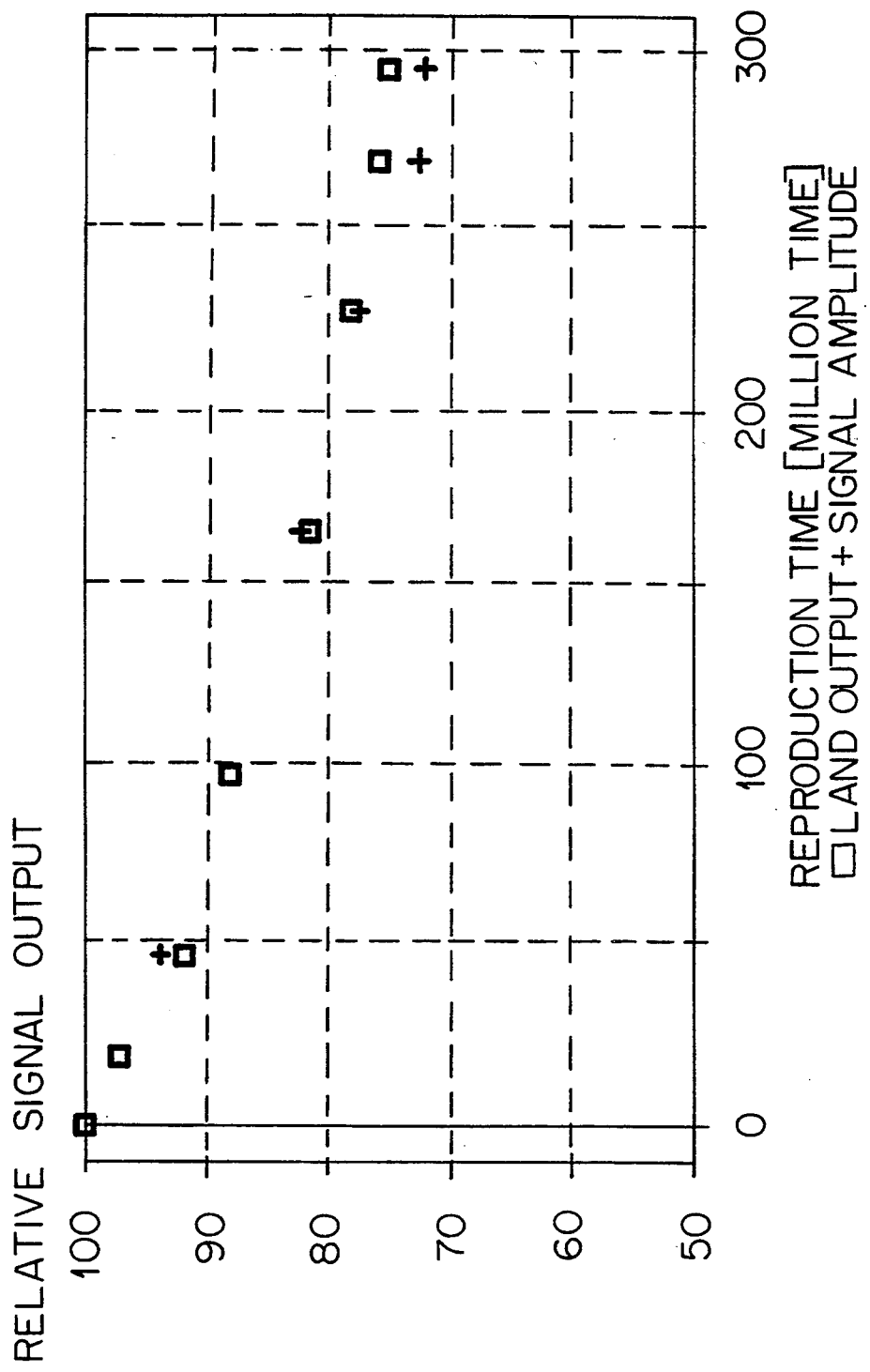
FIG. 11 is a graph showing the relationship between reproduction times and relative signal change in the recording medium obtained in Example 41 when the same track is reproduced 3 million times using the reproducing rays having the light intensity of 0.25 mW/cm² and the change in the reflectance and signal amplitude is measured as the relative signal change.

In order to evaluate the stability of the above recording medium to the reproducing rays, the same track was reproduced 3 million times using the reproducing rays having the light intensity of 25 mW/cm$^2$, and the change in the reflectance and signal amplitude was measured as the signal change. The results are shown in FIG. 11.

EXAMPLE 42

Figure 12:
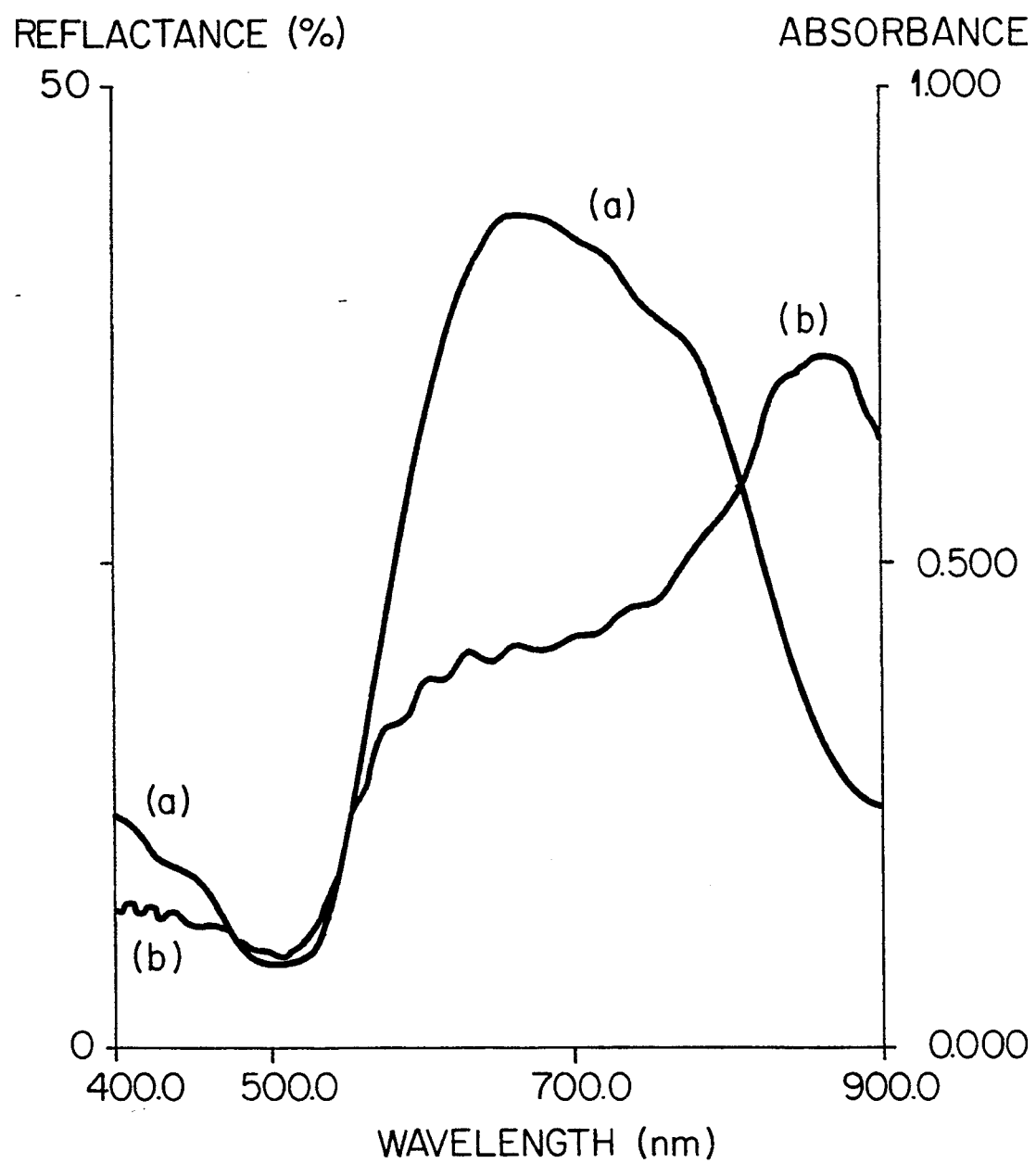
FIG. 12 is a chart showing the spectral properties of the recording medium obtained in Example 42 where the parallel rays are past through the base of the smooth part. (a) shows the absorption spectrum of the recording medium and (b) shows the reflection spectrum where the measuring was carried out through the base of the recording medium.

A recording medium was obtained according to the same manner as that in Example 22 except that the compound obtained in Example 11 was used in place of the compound obtained in Example 1. The spectral properties and recording properties were measured according to the same manner as that in Example 22. The spectral chart is shown in FIG. 12.

EXAMPLE 43

Figure 13:
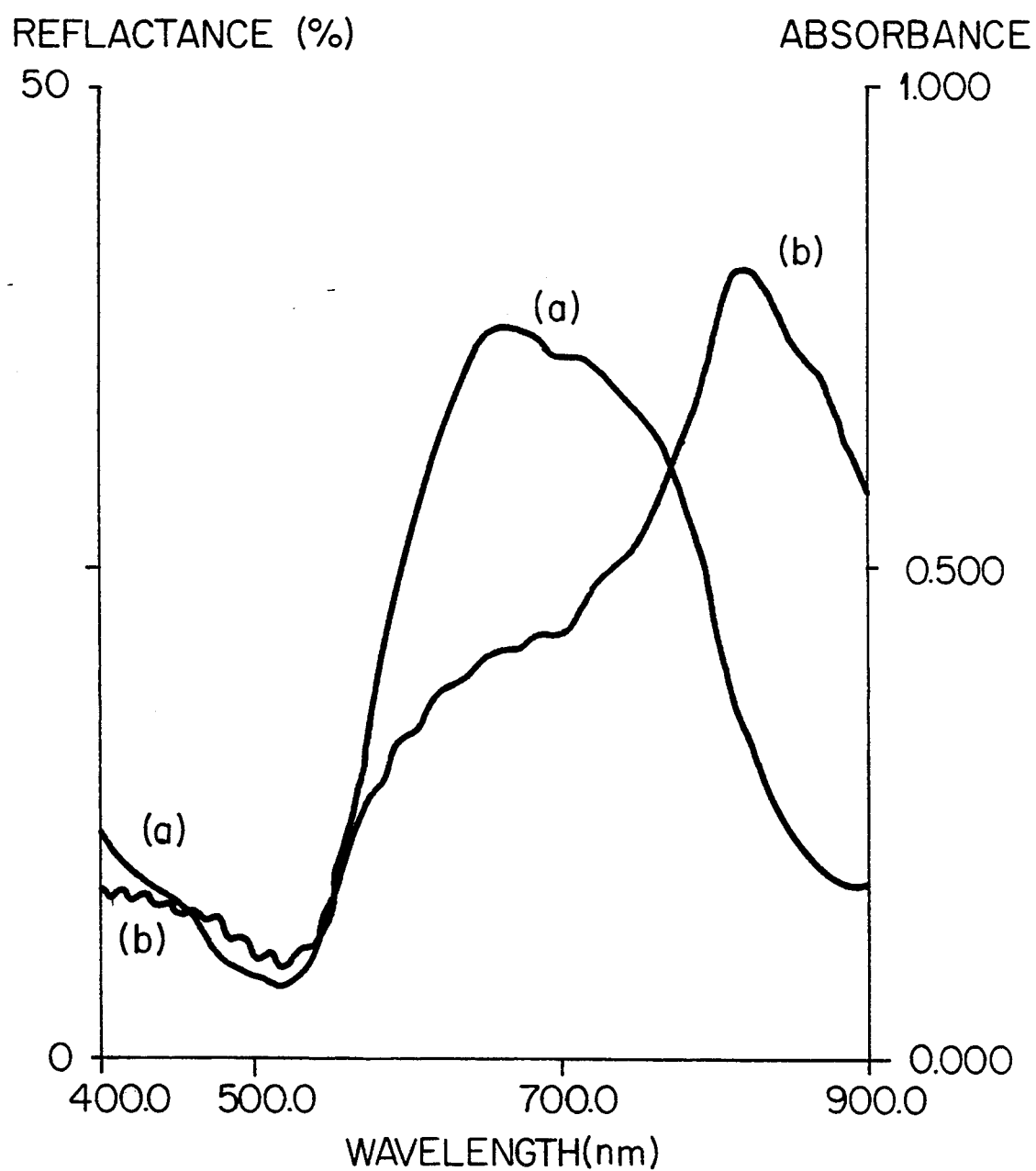
FIG. 13 is a chart showing the spectral properties of the recording medium obtained in Example 43 where the parallel rays are past through the base of the smooth part. (a) shows the absorption spectrum of the recording medium and (b) shows the reflection spectrum where the measuring was carried out through the base of the recording medium.

A recording medium was obtained according to the same manner as that in Example 22 except that the compound obtained in Example 12 was used in place of the compound obtained in Example 1. The spectral properties and recording properties of the resulting recording medium were measured according to the same manner as that in Example 22. The spectral chart is shown in FIG. 13.

EXAMPLE 44

Figure 14:
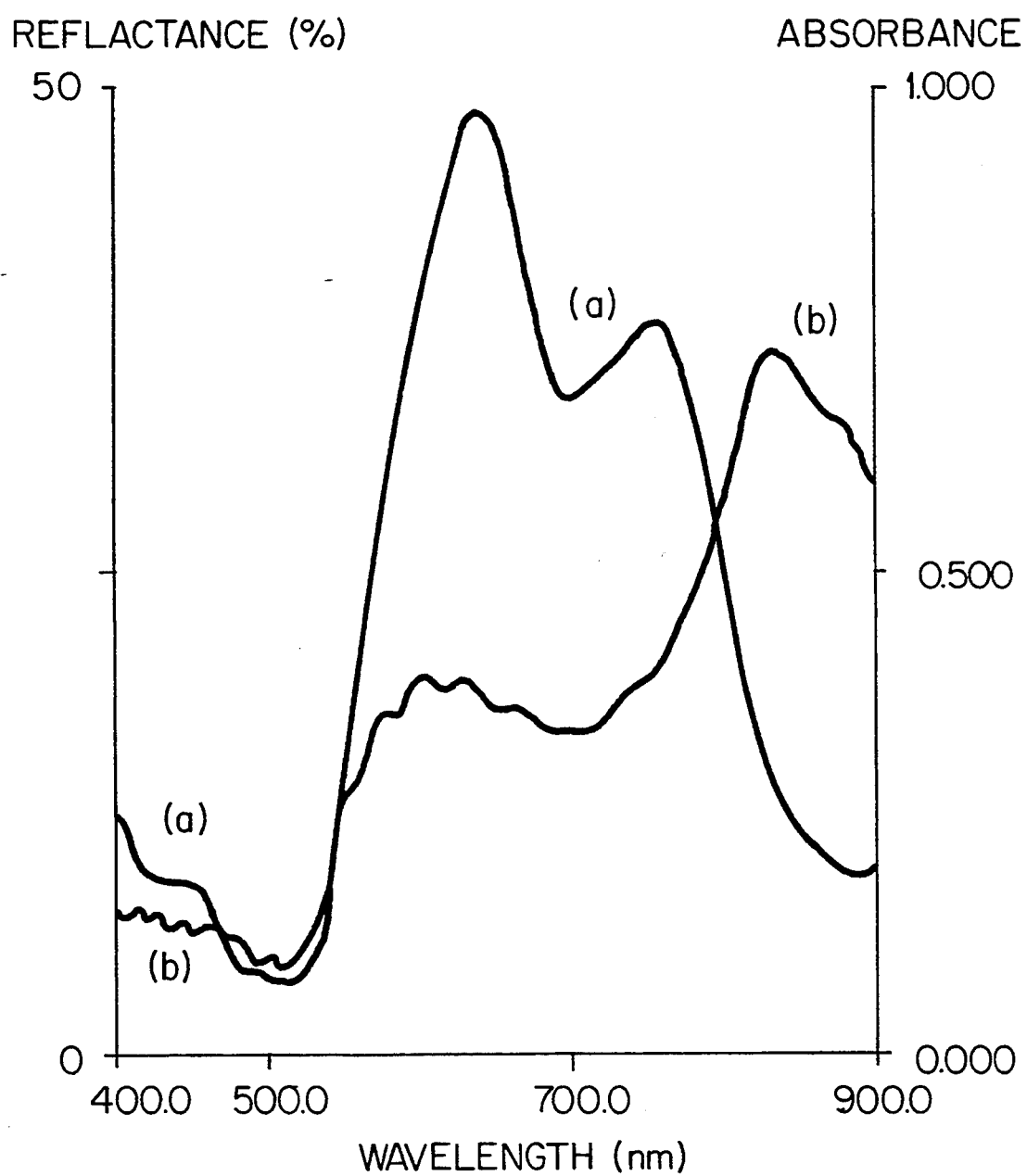
FIG. 14 is a chart showing the spectral properties of the recording medium obtained in Example 44 where the parallel rays are past through the base of the smooth part. (a) shows the absorption spectrum of the recording medium and (b) shows the reflection spectrum where the measuring was carried out through the base of the recording medium.

A recording medium was obtained according to the same manner as that in Example 22 except that the compound obtained in Example 16 was used in place of the compound obtained in Example 1. The spectral properties and recording properties of the resulting recording medium were measured according to the same manner as that in Example 22. The spectral chart is shown in FIG. 14.

EXAMPLE 45

Figure 15:
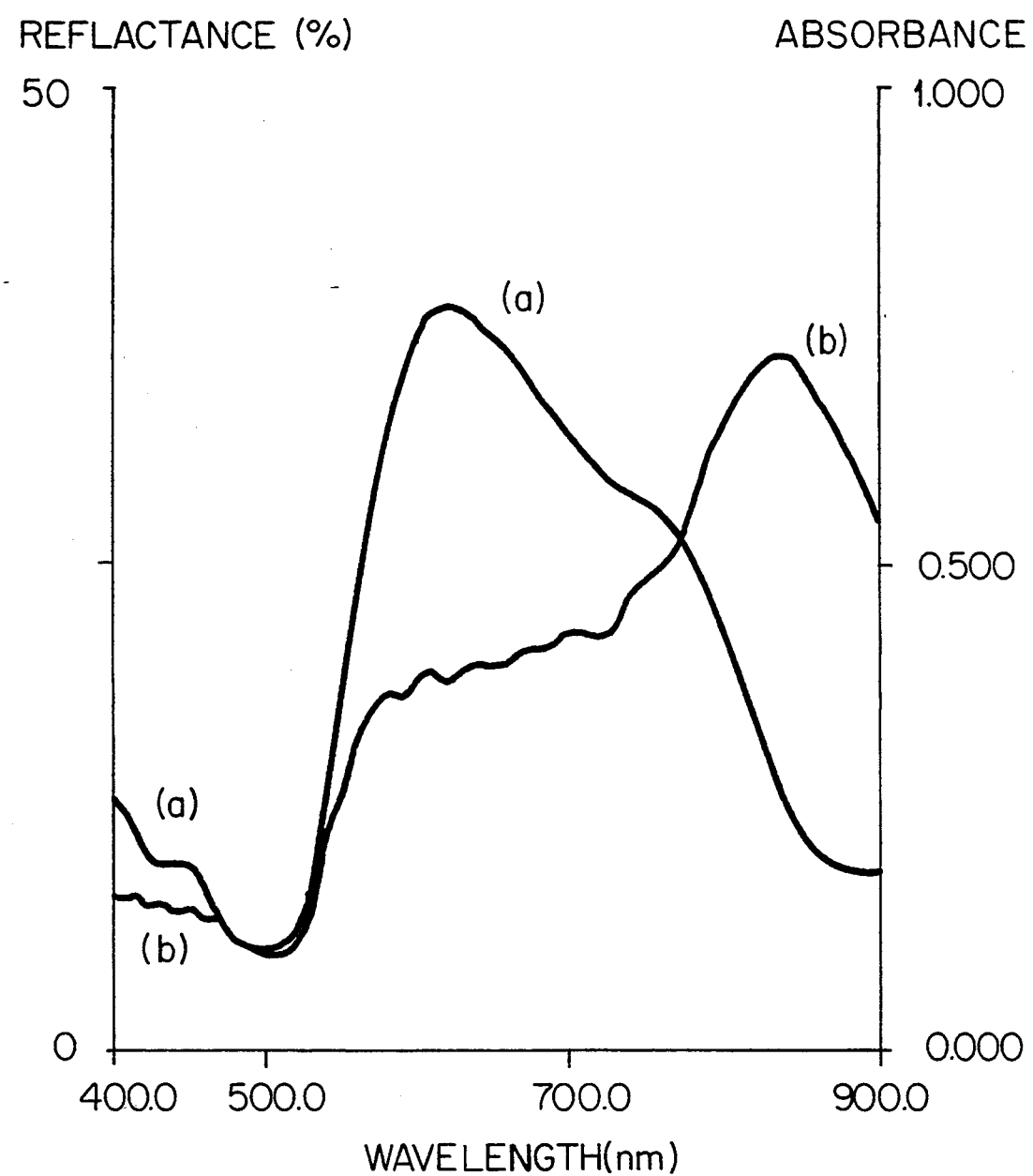
FIG. 15 is a chart showing the spectral properties of the recording medium obtained in Example 45 where the parallel rays are past through the base of the smooth part. (a) shows the absorption spectrum of the recording medium and (b) shows the reflection spectrum where the measuring was carried out through the base of the recording medium.

A recording medium was obtained according to the same manner as that in Example 22 except that the compound obtained in Example 17 was used in place of the compound obtained in Example 1. The spectral properties and recording properties of the resulting recording medium were measured according to the same manner as that in Example 22. The spectral chart is shown in FIG. 15.

EXAMPLE 46

Figure 16:
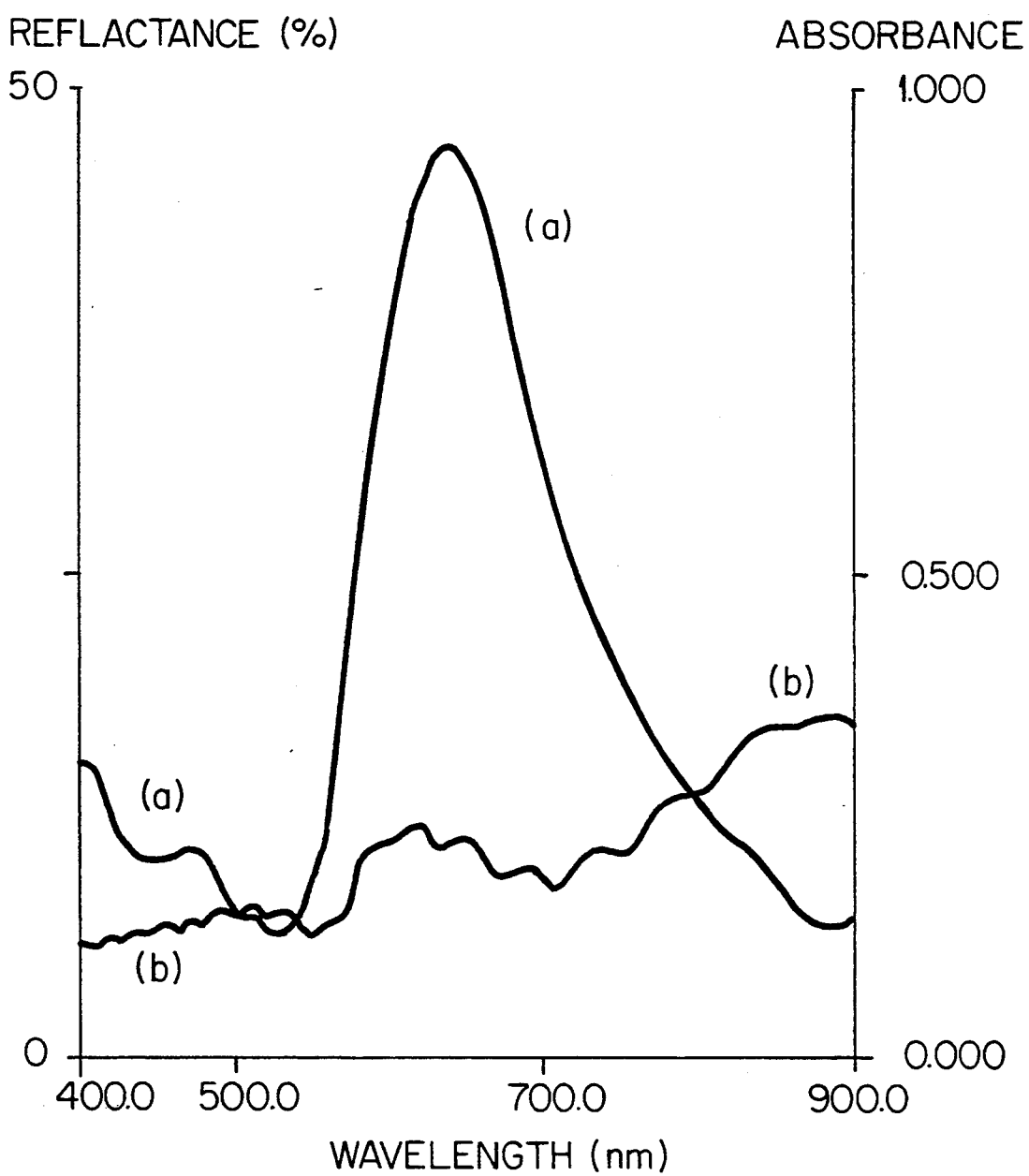
FIG. 16 is a chart showing the spectral properties of the recording medium obtained in Example 46 where the parallel rays are past through the base of the smooth part. (a) shows the absorption spectrum of the recording medium and (b) shows the reflection spectrum where the measuring was carried out through the base of the recording medium.

A recording medium was obtained according to the same manner as that in Example 22 except that the compound obtained in Example 19 was used in place of the compound obtained in Example 1. The spectral properties and recording properties of the resulting recording medium were measured according to the same manner as that in Example 22. The spectral chart is shown in FIG. 16.

EXAMPLE 47

Figure 17:
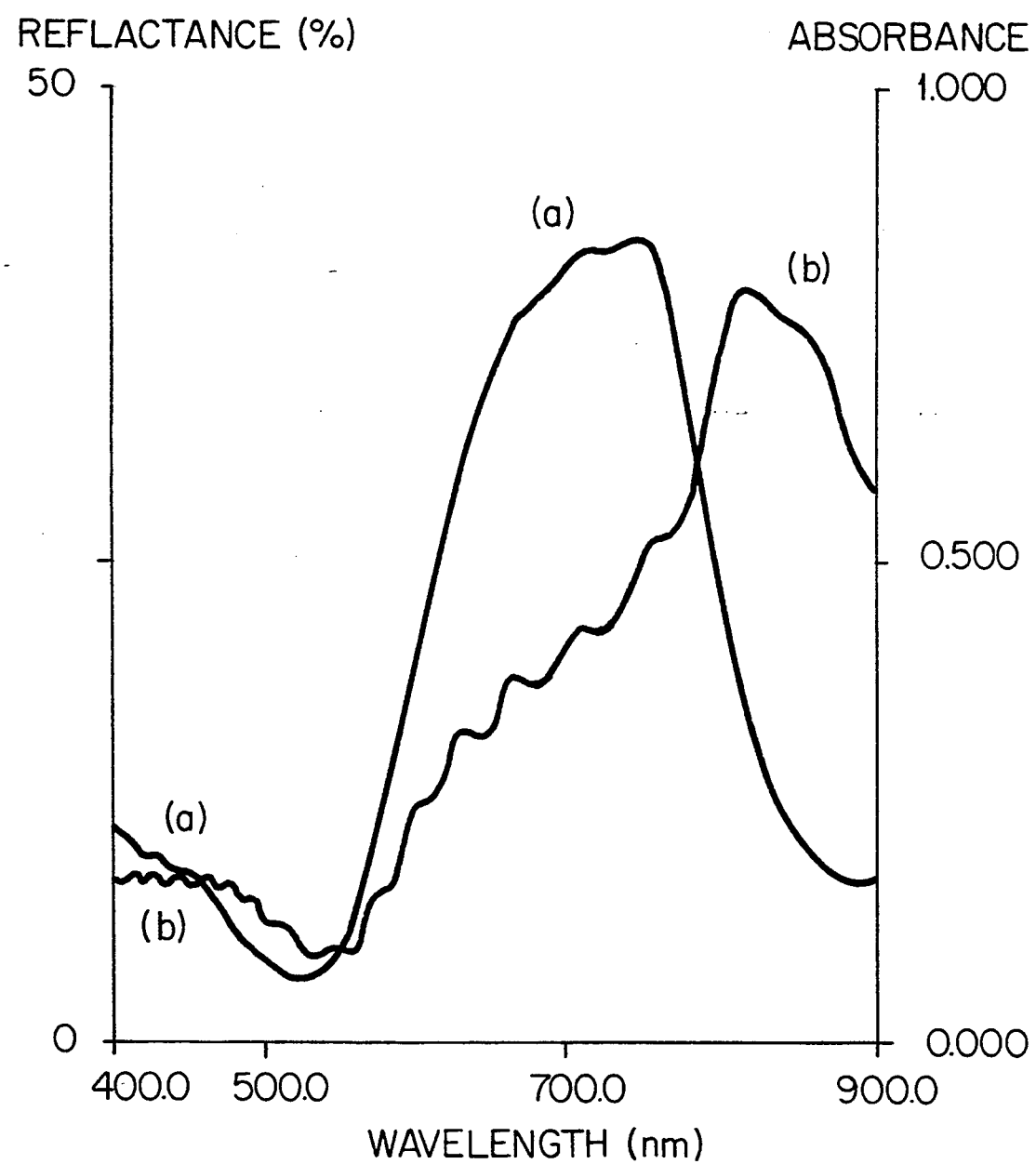
FIG. 17 is a chart showing the spectral properties of the recording medium obtained in Example 47 where the parallel rays are past through the base of the smooth part. (a) shows the absorption spectrum of the recording medium and (b) shows the reflection spectrum where the measuring was carried out through the base of the recording medium.

A recording medium was obtained according to the same manner as that in Example 22 except that the compound obtained in Example 18 was used in place of the compound obtained in Example 1. The spectral properties and recording properties of the resulting recording medium were measured according to the same manner as that in Example 22. The spectral chart is shown in FIG. 17.

EXAMPLE 48

A recording medium was obtained according to the same manner as that in Example 22 except that the compound obtained in Example 20 was used in place of the compound obtained in Example 1. The recording properties of the resulting recording medium were measured according to the same manner as that in Example 22. The spectral chart is shown in Table 1.

EXAMPLE 49

A recording medium was obtained according to the same manner as that in Example 25 except that the compound obtained in Example 18 was used in place of the compound obtained in Example 1. The recording properties of the resulting recording medium were measured according to the same manner as that in Example 22. The spectral chart is shown in Table 1.

EXAMPLE 50

Figure 18:
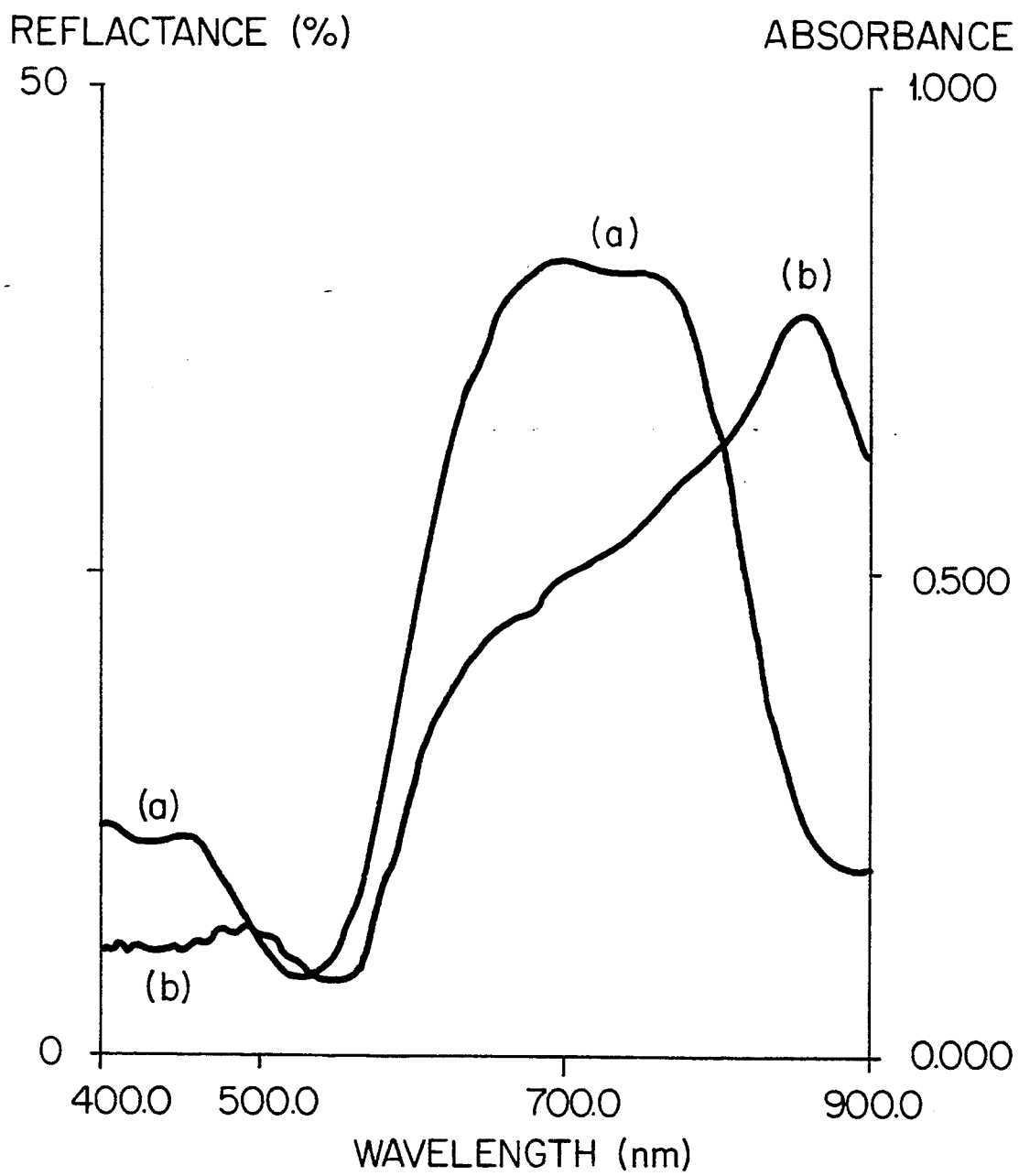
FIG. 18 is a chart showing the spectral properties of the recording medium obtained in Example 50 where the parallel rays are past through the base of the smooth part. (a) shows the absorption spectrum of the recording medium and (b) shows the reflection spectrum where the measuring was carried out through the base of the recording medium.

A recording medium was obtained according to the same manner as that in Example 27 except that the compound obtained in Example 20 was used in place of the compound obtained in Example 3. The spectral properties and recording properties of the resulting recording medium were measured according to the same manner as that in Example 22. The spectral chart is shown in FIG. 18 and the recording properties are shown in Table 1.

EXAMPLE 51

Figure 19:
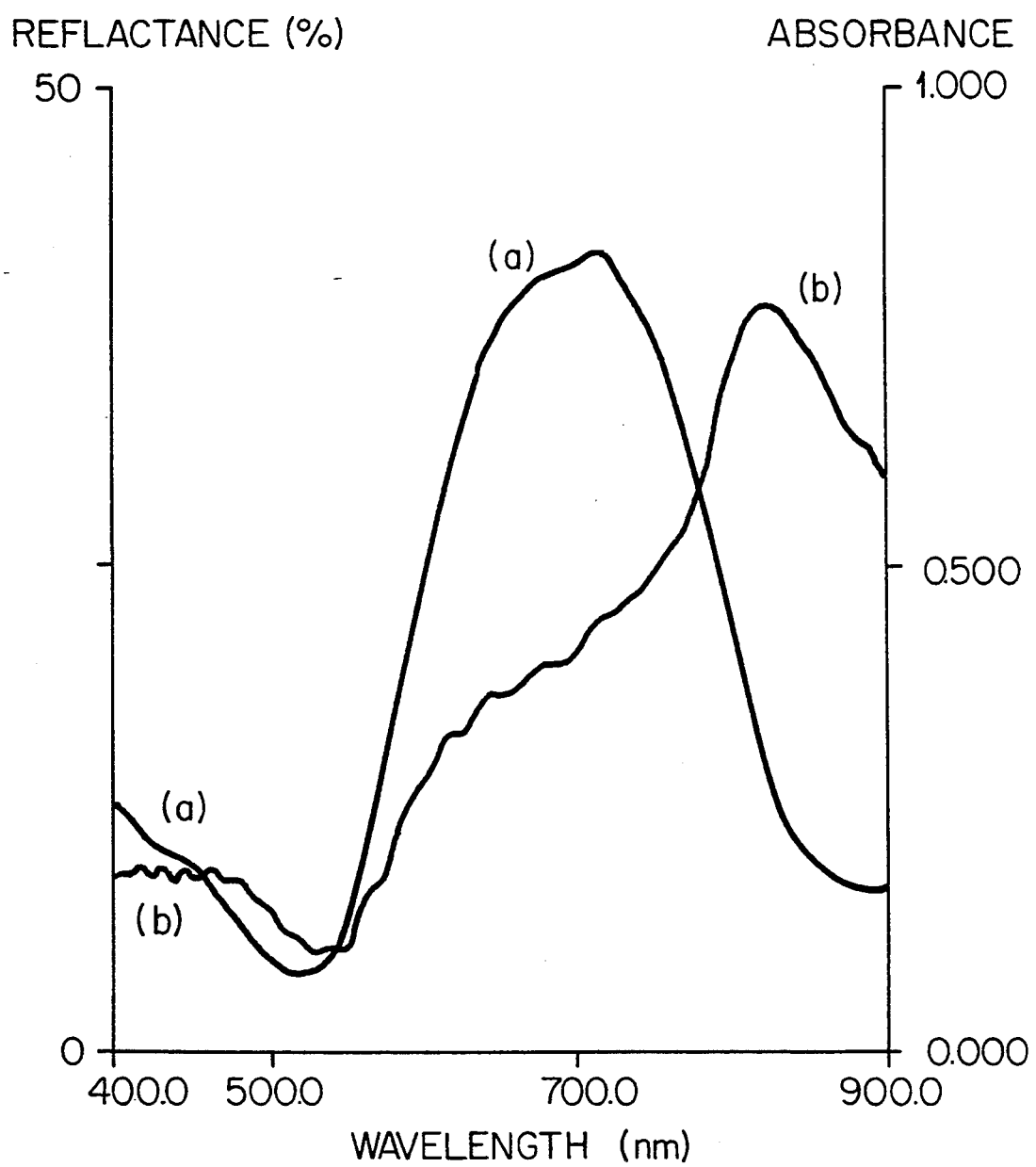
FIG. 19 is a chart showing the spectral properties of the recording medium obtained in Example 51 where the parallel rays are past through the base of the smooth part. (a) shows the absorption spectrum of the recording medium and (b) shows the reflection spectrum where the measuring was carried out through the base of the recording medium.

A recording medium was obtained according to the same manner as that in Example 27 except that the compound obtained in Example 14 was used in place of the compound obtained in Example 3. The spectral properties and recording properties of the resulting recording medium were measured according to the same manner as that in Example 36. The spectral chart is shown in FIG. 19 and the recording properties are shown in Table 1.

EXAMPLE 52

A recording medium was obtained according to the same manner as that in Example 27 except that the compound obtained in Example 15 was used in place of the compound obtained in Example 3. The recording properties of the resulting recording medium were measured according to the same manner as that in Example 22. The recording properties are shown in Table 1.

EXAMPLE 53

A recording medium was obtained according to the same manner as that in Example 26 except that the compound obtained in Example 20 was used in place of the compound obtained in Example 1. The recording properties of the resulting recording medium were measured according to the same manner as that in Example 22. The recording properties are shown in Table 1.

EXAMPLES 54 AND 55

Figure 20:
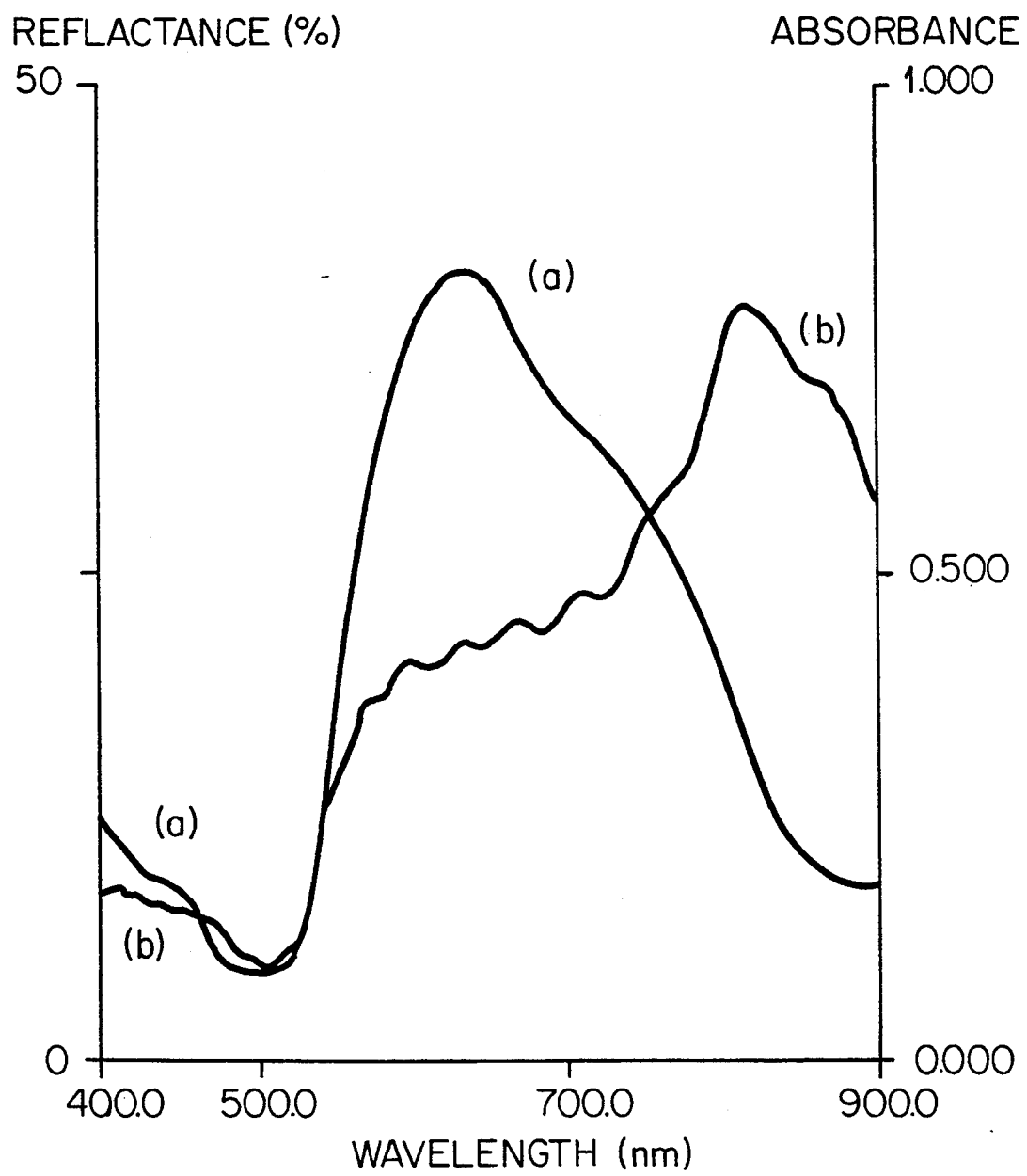
FIG. 20 is a chart showing the spectral properties of the recording medium obtained in Example 54 where the parallel rays are past through the base of the smooth part. (a) shows the absorption spectrum of the recording medium and (b) shows the reflection spectrum where the measuring was carried out through the base of the recording medium.
Figure 21:
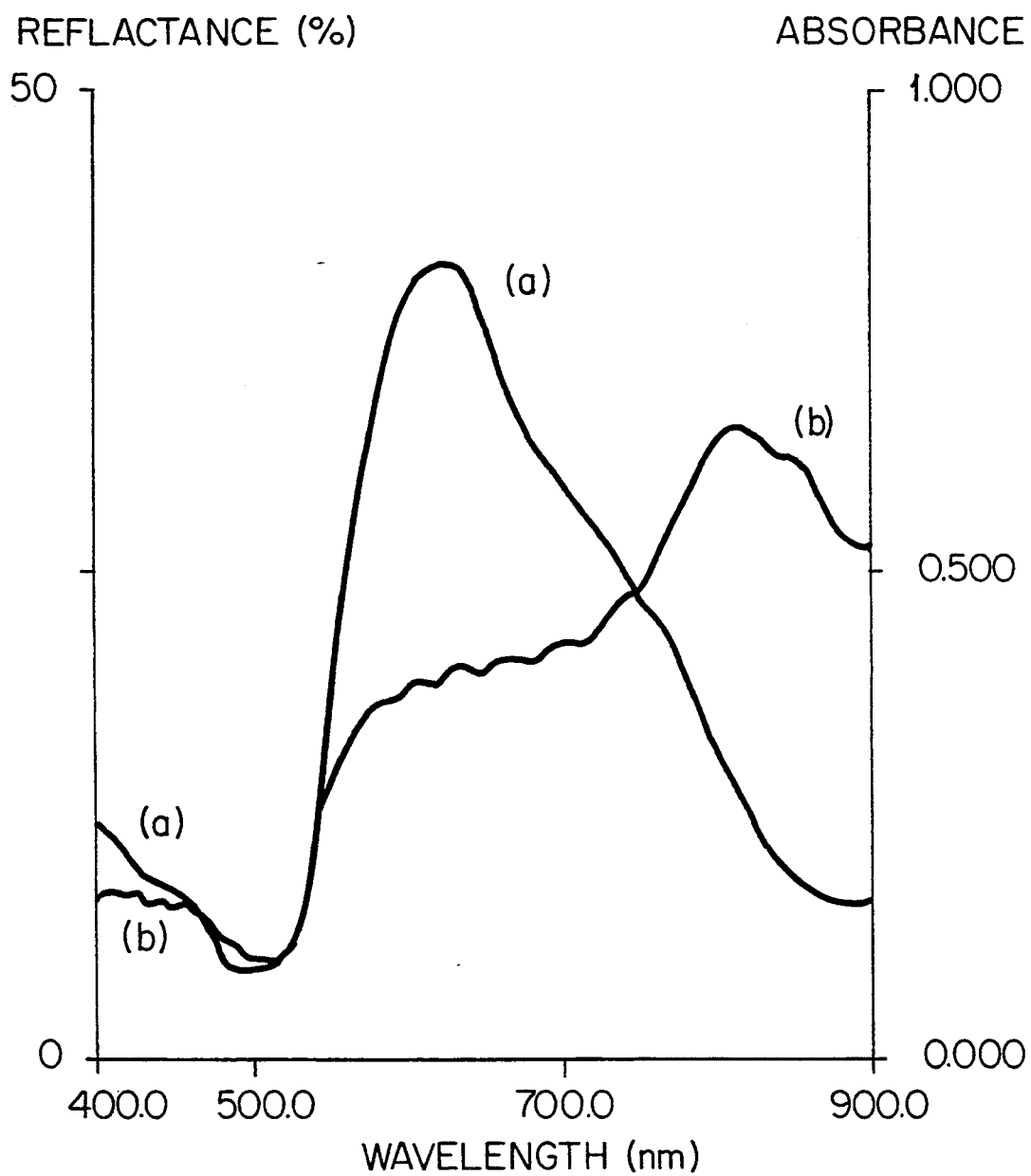
FIG. 21 is a chart showing the spectral properties of the recording medium obtained in Example 55 where the parallel rays are past through the base of the smooth part. (a) shows the absorption spectrum of the recording medium and (b) shows the reflection spectrum where the measuring was carried out through the base of the recording medium.

The corresponding recording media were obtained according to the same manner as that in Example 22 except that a mixture (weight ratio=1/1) of the compound obtained in Example 11 or 14 and a squarylium compound represented by the formula below was used. The spectral properties and recording properties of the resulting recording media were measured according to the same manner as that in Example 22. The spectral charts are shown FIGS. 20 and 21 and the recording properties are shown in Table 1.

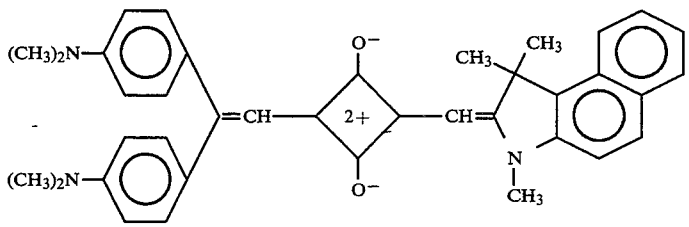

EXAMPLES 56, 57 AND 58

A recording layer having the thickness of 1600 Å was provided by spin-coating a 1,1,2-trifluoroethanol solution containing 4 wt. % of a compound obtained in Example 11, 16 or 19 on an injection molded polycarbonate circular disc having the thickness of 1.2 mm and the diameter of 120 mm. The reflecting layer having the thickness of 1000 Å was provided on the recording layer by gold sputtering under $10^{-5}$ torr, and the protecting layer composed of the ultraviolet-curing resin having the thickness of about 5 μm was provided thereon to give a recording medium. CD format signal was recorded on or reproduced from the resulting recording medium using the semiconductor laser rays having the wavelength of 782 nm and NA of 0.5 under the condition of linear velocity of 1.3 mm/sec, and the reflectance and modulation degree were measured. The results are shown in Table 2.

EXAMPLE 59

Figure 22:
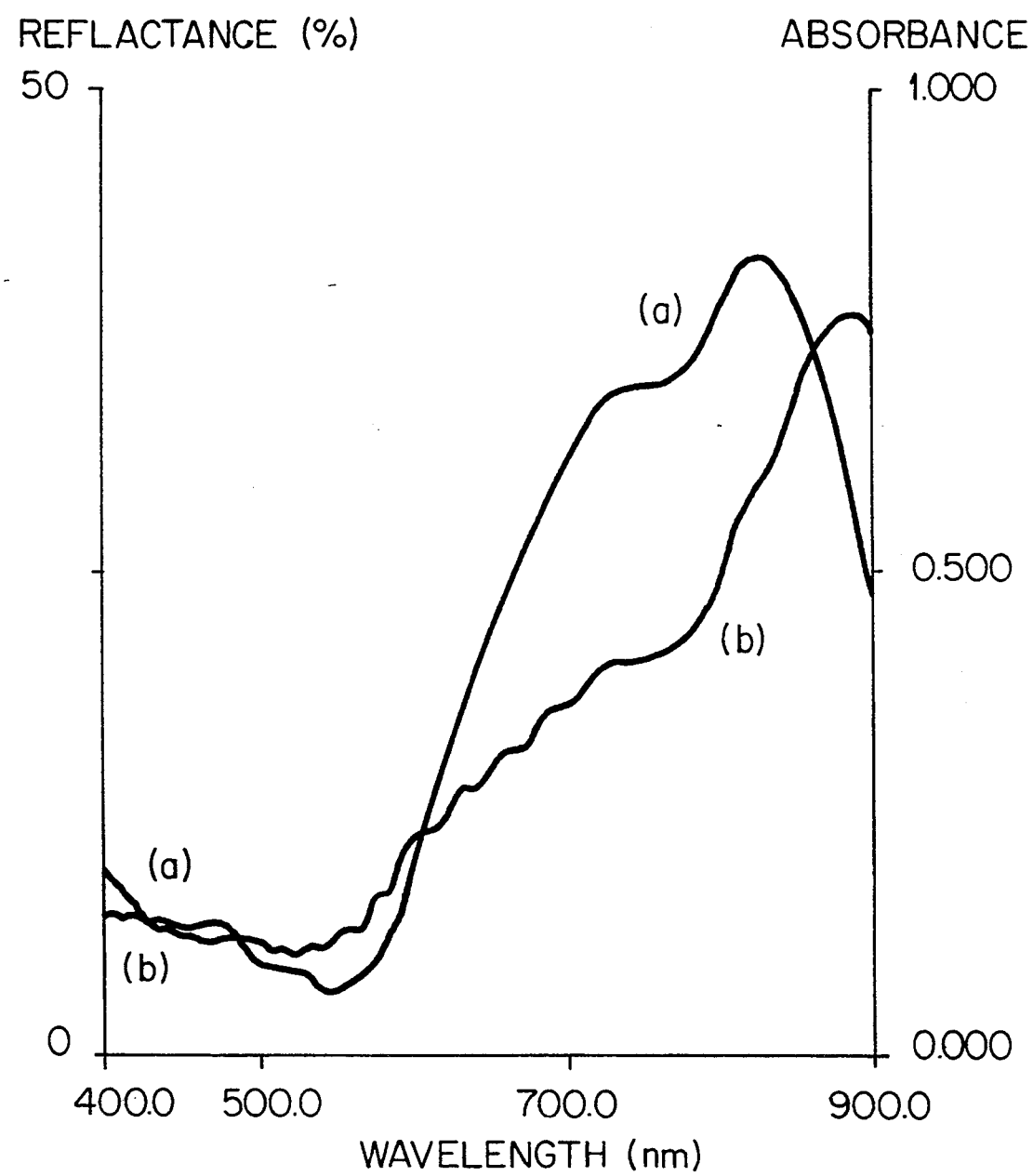
FIG. 22 is a chart showing the spectral properties of the recording medium obtained in Example 59 where the parallel rays are past through the base of the smooth part. (a) shows the absorption spectrum of the recording medium and (b) shows the reflection spectrum where the measuring was carried out through the base of the recording medium.

A recording medium was obtained according to the same manner as that in Example 22 except that the compound obtained in Example 21 was used in place of the compound obtained in Example 1. The spectral properties and recording properties of the resulting recording medium was measured according to the same manner as that in Example 22. The spectral chart is shown is FIG. 22 and the recording properties are shown in Table 1.

EXAMPLE 60

A recording medium was obtained according to the same manner as that in Example 25 except that the compound obtained in Example 21 was used in place of the compound obtained in Example 1. The recording properties of the resulting recording medium was measured according to the same manner as that in Example 22. The recording properties are shown in Table 1.

EXAMPLE 61

A recording medium was obtained according to the same manner as that in Example 26 except that the compound obtained in Example 21 was used in place of the compound obtained in Example 1. The recording properties of the resulting recording medium was measured according to the same manner as that in Example 22. The recording properties are shown in Table 1.

EXAMPLE 62

A recording medium was obtained according to the same manner as that in Example 27 except that the compound obtained in Example 21 was used in place of the compound obtained in Example 3. The recording properties of the resulting recording medium was measured according to the same manner as that in Example 22. The recording properties are shown in Table 1.

EXAMPLE 63

A recording medium was obtained according to the same manner as that in Example 28 except that the compound obtained in Example 21 was used in place of the compound obtained in Example 1. The recording properties of the resulting recording medium were measured according to the same manner as that in Example 22. The recording properties are shown in Table 1.

COMPARATIVE EXAMPLES 1 TO 3

The corresponding recording medium was obtained according to the same manner as that in Example 22 except that (i) cyanin compound, (ii) pyrylium compound, or (iii) naphthoquinone compound represented by the formula (a) to (c) below was used respectively as the recording medium in place of the compound obtained in Example 1. The recording properties of these recording media were measured according to the same manner as that in Example 22. The results are shown in Table 1.

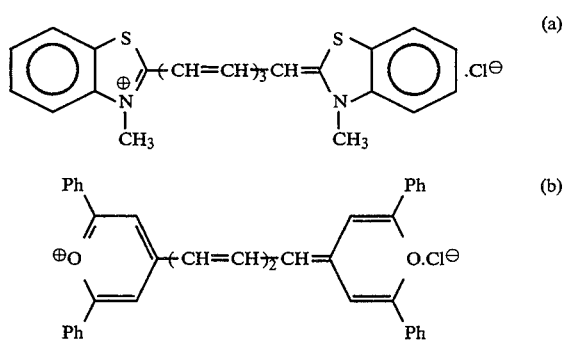

-continued (c) 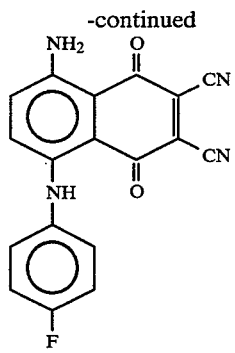

TABLE 1

| Ex. | Initial value Reflectance (%) | Initial value C/N (dB) | Reproduction deterioration-accelerated test Reflectance (%) | Reproduction deterioration-accelerated test C/N (dB) | Storage stability-accelerated test Reflectance (%) | Storage stability-accelerated test C/N (dB) |
|---|---|---|---|---|---|---|
| 22 | 32 | 56 | 12 | 40 | 28 | 54 |
| 23 | 37 | 56 | 13 | 41 | 25 | 53 |
| 24 | 40 | 56 | 12 | 40 | 32 | 54 |
| 25 | 31 | 56 | 28 | 54 | 27 | 54 |
| 26 | 30 | 56 | 27 | 54 | 24 | 52 |
| 27 | 26 | 56 | 20 | 52 | 21 | 52 |
| 28 | 33 | 56 | 14 | 53 | 28 | 54 |
| 29 | 23 | 56 | 20 | 53 | 20 | 51 |
| 30 | 24 | 56 | 21 | 53 | 21 | 52 |
| 31 | 23 | 56 | 22 | 54 | 20 | 51 |
| 32 | 22 | 55 | 21 | 53 | 19 | 50 |
| 33 | 25 | 56 | 23 | 54 | 23 | 53 |
| 34 | 26 | 56 | 16 | 49 | 18 | 49 |
| 35 | 25 | 55 | 22 | 53 | 21 | 51 |
| 36 | 22 | 56 | 11 | 37 | 20 | 53 |
| 37 | 22 | 56 | 19 | 52 | 20 | 53 |
| 38 | 21 | 55 | 18 | 51 | 19 | 51 |
| 39 | 20 | 56 | 10 | 35 | 18 | 52 |
| 40 | 24 | 56 | 14 | 42 | 22 | 53 |
| 41 | 30 | 56 | 28 | 54 | 24 | 53 |
| 47 | 34 | 56 | 16 | 48 | 24 | 53 |
| 48 | 24 | 55 | 13 | 40 | 19 | 50 |
| 49 | 33 | 56 | 28 | 54 | 23 | 53 |
| 50 | 23 | 55 | 13 | 41 | 18 | 50 |
| 51 | 30 | 56 | 14 | 42 | 26 | 54 |
| 52 | 28 | 56 | 26 | 53 | 23 | 53 |
| 53 | 22 | 54 | 20 | 52 | 17 | 50 |
| 54 | 28 | 56 | 24 | 55 | 24 | 53 |
| 55 | 26 | 55 | 24 | 54 | 23 | 53 |
| 59 | 24 | 56 | 12 | 36 | 22 | 54 |
| 60 | 24 | 56 | 21 | 53 | 22 | 54 |
| 61 | 23 | 56 | 20 | 52 | 20 | 52 |
| 62 | 23 | 56 | 11 | 35 | 21 | 53 |
| 63 | 26 | 56 | 14 | 42 | 23 | 54 |
| Comp. Ex. | | | | | | |
| 1 | 23 | 55 | 10 | Unmeasurable | 18 | 49 |
| 2 | 18 | 54 | 7 | Unmeasurable | 15 | 43 |
| 3 | 15 | 53 | 14 | 53 | Unmeasurable due to crystallization | |

TABLE 2

| Example | Reflectance (%) | Modulation degree (%) | Maximum recording power (mW) |
|---|---|---|---|
| 56 | 71 | 67 | 6.0 |
| 57 | 68 | 64 | 6.0 |
| 58 | 65 | 63 | 6.5 |

In these Examples, the recorded signals were reproduced using a commercially available CD player.

What is claimed is:

1. A squarylium compound represented by the formula (I):

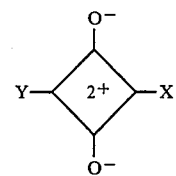

wherein
(1) X represents the group (A):

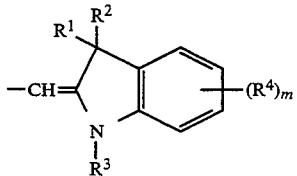

wherein R¹ and R² are the same or different and represent an alkyl group having 1 to 4 carbon atoms, or R¹ and R² together with the carbon atom to which they are bonded form a hydrocarbon ring having 4 to 7 carbon atoms, R³ represents a hydrogen atom, an alkyl group having 1 to 4 carbon atoms or a phenyl group or naphthyl group, R⁴ represents a halogen atom, an alkyl group having 1 to 4 carbon atoms, an aralkyl group having 7 to 10 carbon atoms, a phenyl group or a naphthyl group or an alkoxy group in which the alkyl part has 1 to 4 carbon atoms, m represents an integer of 0 to 4, provided that when m represents 2 to 4, R⁴'s may be the same or different or two adjacent R⁴'s may form an aromatic ring which is unsubstituted or substituted by one or more halogen atoms, alkyl groups having 1 to 4 carbon atoms, aralkyl groups having 7 to 10 carbon atoms, phenyl groups or naphthyl groups, and Y represents the group (B):

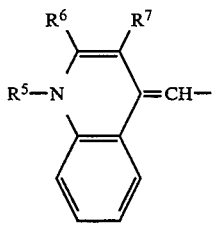

wherein R⁵ represents an alkyl group having 1 to 4 carbon atoms, R⁶ and R⁷ are the same or different and represent a hydrogen atom, an alkyl group having 1 to 4 carbon atoms or an aralkyl group having 7 to 10 carbon atoms, or R⁶ and R⁷ together with the carbon atoms to which they are bonded form an aromatic ring or hydrocarbon ring having 5 to 8 carbon atoms in the ring, said ring being unsubstituted or substituted by one or more halogen atoms, alkyl groups having 1 to 4 carbon atoms, aralkyl groups having 7 to 10 carbon atoms, phenyl groups or naphthyl groups, or (2) X represents the group (C):

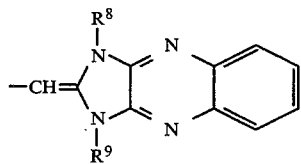

wherein $R^8$ and $R^9$ are the same or different and represent a hydrogen atom, an aralkyl group having 7 to 10 carbon atoms, an alkyl group having 1 to 6 carbon atoms, a cyclic alkyl group having 3 to 8 carbon atoms, a phenyl group or a naphthyl group, and Y represents the group (D):

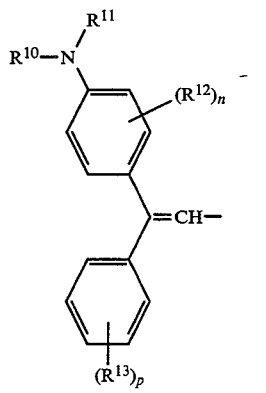

wherein $R^{10}$ and $R^{11}$ are the same or different and represent a hydrogen atom, an alkyl group having 1 to 6 carbon atoms, a cyclic alkyl group having 3 to 8 carbon atoms, an aralkyl group having 7 to 10 carbon atoms or a phenyl group or a naphthyl group, said aralkyl or phenyl group or naphthyl group being unsubstituted or substituted with one or more halogen atoms, alkyl groups having 1 to 6 carbon atoms, cyclic alkyl groups having 3 to 8 carbon atoms, alkoxy groups in which the alkyl part has 1 to 6 carbon atoms or is a cyclic alkyl group having 3 to 8 carbon atoms, aralkyl groups having 7 to 10 carbon atoms, phenyl groups or naphthyl groups, $R^{12}$ represents a halogen atom, an alkyl group having 1 to 6 carbon atoms, a cyclic alkyl group having 3 to 8 carbon atoms, an alkoxy group in which the alkyl part has 1 to 6 carbon atoms or is a cyclic alkyl group having 3 to 8 carbon atoms, a nitro group or a hydroxy group, n represents an integer of 0 to 4 provided that when n represents 2 to 4, $R^{12}$'s are the same or different, $R^{13}$ represents a halogen atom, an alkyl group having 1 to 6 carbon atoms, a cyclic alkyl group having 3 to 8 carbon atoms, an alkoxy group in which the alkyl part has 1 to 6 carbon atoms or is a cyclic alkyl group having 3 to 8 carbon atoms, a hydroxy group, a nitro group, a cyano group, a trifluoromethyl group or $-NQ^1Q^2$ (wherein $Q^1$ and $Q^2$ are the same or different and are as defined for $R^{10}$), p represents an integer of 0 to 5 provided that when p represents 2 to 5, $R^{13}$'s are the same or different, or Y represents the group (E):

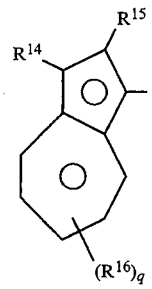

wherein $R^{14}$ and $R^{15}$ represent a hydrogen atom, an alkyl group having 1 to 6 carbon atoms, a cyclic alkyl group having 3 to 8 carbon atoms, an aralkyl group having 7 to 10 carbon atoms or a phenyl group or a naphthyl group, or $R^{14}$ and $R^{15}$ together with the carbon atoms to which they are bonded form an aromatic, heterocyclic or hydrocarbon ring having 5 to 8 atoms in the ring, said ring being unsubstituted or substituted by one or more halogen atoms, alkyl groups having 1 to 6 carbon atoms, cyclic alkyl groups having 3 to 8 carbon atoms, alkoxy groups in which the alkyl part has 1 to 6 carbon atoms or is a cyclic alkyl group having 3 to 8 carbon atoms, aralkyl groups having 7 to 10 carbon atoms, or phenyl groups or naphthyl groups, $R^{16}$ represents an alkyl group having 1 to 6 carbon atoms, a cyclic alkyl group having 3 to 8 carbon atoms, an aralkyl group having 7 to 10 carbon atoms or a phenyl group or a naphthyl group, q represents an integer of 0 to 3 provided that when q represents 2 or 3, $R^{16}$'s are the same or different, or two adjacent $R^{16}$'s together with the carbon atoms to which they are bonded form an aromatic, heterocyclic or hydrocarbon ring having 5 to 8 atoms in the ring, said ring being unsubstituted or substituted by one or more halogen atoms, alkyl groups having 1 to 6 carbon atoms, cyclic alkyl groups having 3 to 8 carbon atoms, alkoxy groups in which the alkyl part has 1 to 6 carbon atoms or is a cyclic alkyl group having 3 to 8 carbon atoms, or Y represents the group (B):

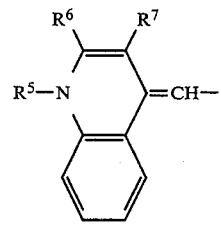

wherein $R^5$, $R^6$ and $R^7$ are the same as defined above.

2. The squarylium compound of claim 1, wherein X represents the group (A):

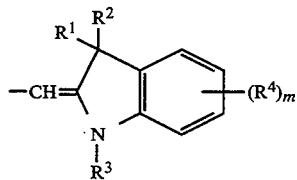

(A)

wherein $R^1$ and $R^2$ are the same or different and represent an alkyl group having 1 to 4 carbon atoms, or $R^1$ and $R^2$ together with the carbon atom to which they are bonded form a hydrocarbon ring having 4 to 7 carbon atoms, $R^3$ represents a hydrogen atom, an alkyl group having 1 to 4 carbon atoms or a phenyl group or naphthyl group, $R^4$ represents a halogen atom, an alkyl group having 1 to 4 carbon atoms, an aralkyl group having 7 to 10 carbon atoms, a phenyl group or a naphthyl group or an alkoxy group in which the alkyl part has 1 to 4 carbon atoms, m represents an integer of 0 to 4, provided that when m represents 2 to 4, $R^4$'s may be the same or different or two adjacent $R^4$'s may form an aromatic ring which is unsubstituted or substituted by one or more halogen atoms, alkyl groups having 1 to 4 carbon atoms, aralkyl groups having 7 to 10 carbon atoms, phenyl groups or naphthyl groups, and Y represents the group (B):

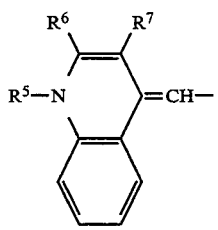

(B)

wherein $R^5$ represents an alkyl group having 1 to 4 carbon atoms, $R^6$ and $R^7$ are the same or different and represent a hydrogen atom, and alkyl group having 1 to 4 carbon atoms or an aralkyl group having 7 to 10 carbon atoms, or $R^6$ and $R^7$ together with the carbon atoms to which they are bonded form an aromatic ring or hydrocarbon ring having 5 to 8 carbon atoms in ring, said ring being unsubstituted or substituted by one or more halogen atoms, alkyl groups having 1 to 4 carbon atoms, aralkyl groups having 7 to 10 carbon atoms, phenyl groups or naphthyl groups.

3. The squarylium compound according to claim 1, wherein X represents the group (C):

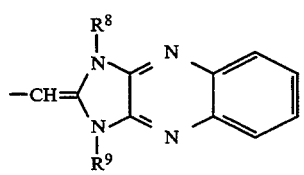

(C)

wherein $R^8$ and $R^9$ are the same or different and represent a hydrogen atom, an aralkyl group having 7 to 10 carbon atoms, an alkyl group having 1 to 6 carbon atoms, a cyclic alkyl group having 3 to 8 carbon atoms, a phenyl group or a naphthyl group, and Y represents the group (D):

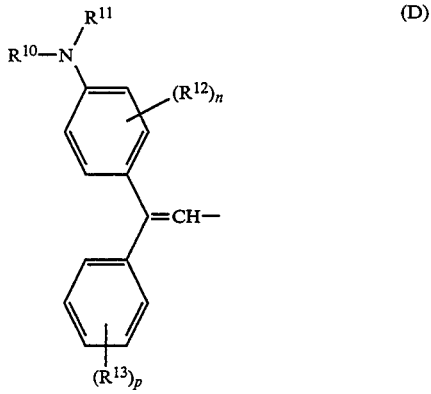

(D)

wherein $R^{10}$ and $R^{11}$ are the same or different and represent a hydrogen atom, an alkyl group having 1 to 6 carbon atoms, a cyclic alkyl group having 3 to 8 carbon atoms, an aralkyl group having 7 to 10 carbon atoms or a phenyl group or a naphthyl group, said aralkyl or phenyl group or naphthyl group being unsubstituted or substituted with one or more halogen atoms, alkyl groups having 1 to 6 carbon atoms, cyclic alkyl groups having 3 to 8 carbon atoms, alkoxy groups in which the alkyl part has 1 to 6 carbon atoms or is a cyclic alkyl group having 3 to 8 carbon atoms, aralkyl groups having 7 to 10 carbon atoms, phenyl groups or naphthyl groups, $R^{12}$ represents a halogen atom, an alkyl group having 1 to 6 carbon atoms, a cyclic alkyl group having 3 to 8 carbon atoms, an alkoxy group in which the alkyl part has 1 to 6 carbon atoms or is a cyclic alkyl group having 3 to 8 carbon atoms, a nitro group or a hydroxy group, n represents an integer of 0 to 4 provided that when n represents 2 to 4, $R^{13}$'s are the same or different, $R^{13}$ represents a halogen atom, an alkyl group having 1 to 6 carbon atoms, a cyclic alkyl group having 3 to 8 carbon atoms, an alkoxy group in which the alkyl part has 1 to 6 carbon atoms or is a cyclic alkyl group having 3 to 8 carbon atoms, a hydroxy group, a nitro group, a cyano group, a trifluoromethyl group or —$NQ^1Q^2$ (wherein $Q^1$ and $Q^2$ are the same or different and are as defined for $R^{10}$), p represents an integer of 0 to 5 provided that when p represents 2 to 5, $R^{13}$'s are the same or different, or Y represents the group (E):

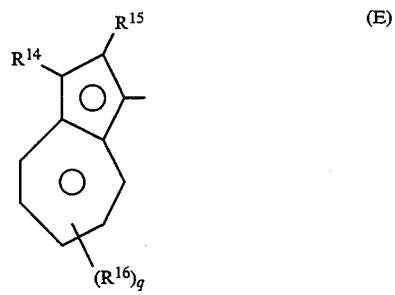

(E)

wherein $R^{14}$ and $R^{15}$ represents a hydrogen atom, an alkyl group having 1 to 6 carbon atoms, a cyclic alkyl group having 3 to 8 carbon atoms, an aralkyl group having 7 to 10 carbon atoms or a phenyl group or a naphthyl group, or $R^{14}$ and $R^{15}$ together with the carbon atoms to which they are bonded form an aromatic, heterocyclic or hydrocarbon ring having 5 to 8 atoms in the ring, said ring being unsubstituted or substituted by one or more halogen atoms, alkyl groups having 1 to 6 carbon atoms, cyclic alkyl groups having 3 to 8 carbon atoms, alkoxy groups in which the alkyl part has 1 to 6 carbon atoms, or is a cyclic alkyl group having 3 to 8 carbon atoms, aralkyl groups having 7 to 10 carbon atoms, or phenyl groups or naphthyl groups, $R^{16}$ represents an alkyl group having 1 to 6 carbon atoms, a cyclic alkyl group having 3 to 8 carbon atoms, an aralkyl group having 7 to 10 carbon atoms or a phenyl group or a naphthyl group, q represents an integer of 0 to 3 provided that when q represents 2 or 3, $R^{13}$'s are the same or different, or two adjacent $R^{16}$'s together with the carbon atoms to which they are bonded form an aromatic, heterocyclic or hydrocarbon ring having 5 to 8 atoms in the ring, said ring being unsubstituted or substituted by one or more halogen atoms, alkyl groups having 1 to 6 carbon atoms, cyclic alkyl groups having 3 to 8 carbon atoms, alkoxy groups in which the alkyl part has 1 to 6 carbon atoms or is a cyclic alkyl group having 3 to 8 carbon atoms, or Y represents the group (B):

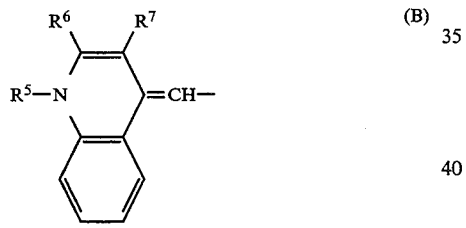

wherein $R^5$, $R^6$ and $R^7$ are the same as defined above.

4. The squarylium compound according to claim 2, wherein said alkyl group and the alkyl part of said alkoxy group a straight or branched alkyl chain having 1 to 4 carbon atoms, and said aromatic ring is a benzene ring which is unsubstituted or substituted by one or more halogen atoms, alkyl groups having 1 to 4 carbon atoms, aralkyl groups having 7 to 10 carbon atoms, phenyl groups or naphthyl groups.

5. The squarylium compound according to claim 3, wherein said alkyl group and the alkyl part of said alkoxy group a straight or branched alkyl chain having 1 to 6 carbon atoms or a cyclic alkyl group having 3 to 8 carbon atoms in the ring, said aralkyl group is unsubstituted or substituted by one or more halogen atoms, alkyl groups or alkoxy groups, said aryl group is unsubstituted or substituted by one or more halogen atoms, alkyl groups or alkoxy groups, said aromatic ring is a benzene ring which is unsubstituted or substituted by one or more halogen atoms, alkyl groups, aralkyl groups, phenyl groups or naphthyl groups, and the heterocyclic ring formed by $R^{14}$ and $R^{15}$ or the adjacent $R^{16}$'s is selected from the group consisting of: —CH=CH—O—, —N=CH—S— and —CH=CH—S—.

6. The squarylium compound according to claim 2, which is:

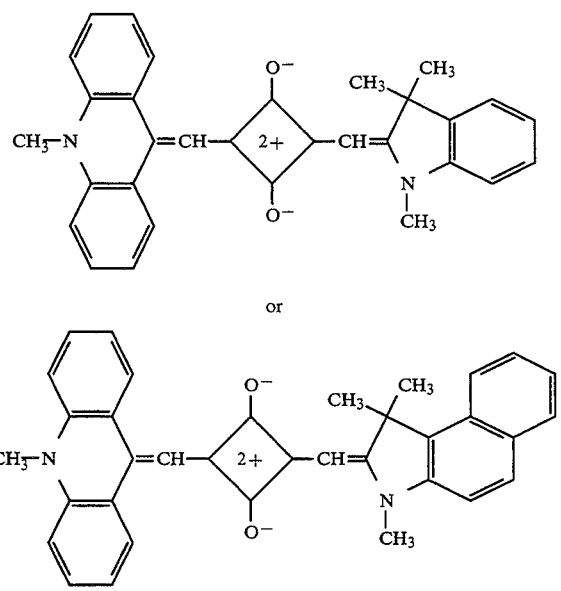

7. The squarylium compound according to claim 3, which is:

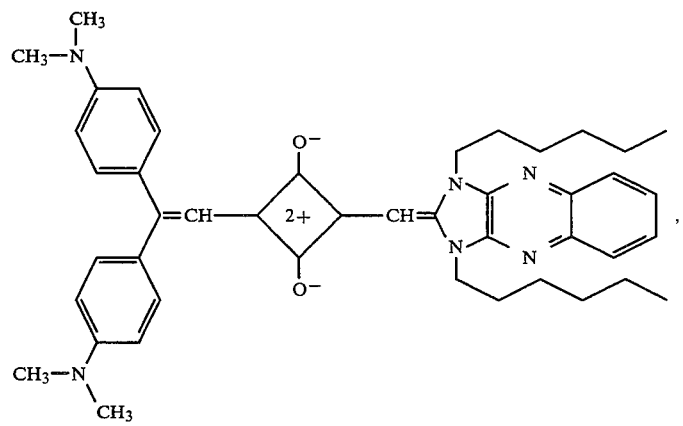

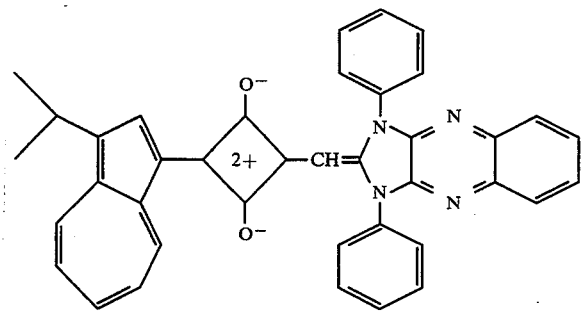
or
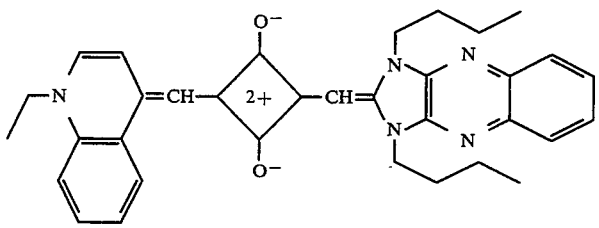
* * * * *

UNITED STATES PATENT AND TRADEMARK OFFICE
CERTIFICATE OF CORRECTION

PATENT NO. : 5,391,741
DATED : February 21, 1995
INVENTOR(S) : Ikuo SHIMIZU et al.

It is certified that error appears in the above-indentified patent and that said Letters Patent is hereby corrected as shown below:

On the title page, item [73] "Assignee", insert --; Ricoh Company, Ltd., both of-- after "Kyowa Hakko Kogyo Co., Ltd.".

Signed and Sealed this

Second Day of July, 1996

Attest:

BRUCE LEHMAN

Attesting Officer

Commissioner of Patents and Trademarks